US008440701B2

(12) United States Patent
Thuring et al.

(10) Patent No.: US 8,440,701 B2
(45) Date of Patent: *May 14, 2013

(54) TRISUBSTITUTED 1,2,4 TRIAZOLES

(75) Inventors: Johannes Wilhelmus John F. Thuring, Antwerp (BE); Theodorus Dinklo, Beerse (BE); Anne Simone Josephine Lesage, Halle-Zoersel (BE); Marcel Frans Leopold De Bruyn, Wortel (BE); Wei Zhuang, Antwerp (BE)

(73) Assignee: Janssen Pharmaceutica NV, Beerse (BE)

( * ) Notice: Subject to any disclaimer, the term of this patent is extended or adjusted under 35 U.S.C. 154(b) by 116 days.

This patent is subject to a terminal disclaimer.

(21) Appl. No.: 12/738,763

(22) PCT Filed: Oct. 15, 2008

(86) PCT No.: PCT/EP2008/063845
§ 371 (c)(1),
(2), (4) Date: Apr. 19, 2010

(87) PCT Pub. No.: WO2009/050186
PCT Pub. Date: Apr. 23, 2009

(65) Prior Publication Data
US 2010/0216846 A1  Aug. 26, 2010

(30) Foreign Application Priority Data
Oct. 18, 2007  (EP) .................................. 07118825

(51) Int. Cl.
A61K 31/4439  (2006.01)
C07D 401/04  (2006.01)
(52) U.S. Cl.
USPC ........................................ 514/340; 546/272.4
(58) Field of Classification Search . 546/272.4; 514/340
See application file for complete search history.

(56) References Cited

U.S. PATENT DOCUMENTS

| 3,933,838 A | 1/1976 | Manghisi et al. |
| 6,187,797 B1 | 2/2001 | Pruitt et al. |
| 6,569,874 B1 | 5/2003 | Pruitt et al. |
| 8,143,419 B2 | 3/2012 | Thuring et al. |
| 2004/0073029 A1 | 4/2004 | Pruitt et al. |
| 2004/0254236 A1 | 12/2004 | Dong et al. |
| 2005/0004134 A1 | 1/2005 | Tsutsumi et al. |
| 2006/0063756 A1 | 3/2006 | Salituro et al. |
| 2010/0240707 A1 | 9/2010 | Thuring et al. |
| 2010/0324053 A1 | 12/2010 | Macdonald et al. |
| 2011/0065683 A1 | 3/2011 | Thuring et al. |
| 2011/0269748 A1 | 11/2011 | Thuring et al. |
| 2012/0172354 A1 | 7/2012 | Macdonald et al. |
| 2012/0238561 A1 | 9/2012 | Macdonald et al. |

FOREIGN PATENT DOCUMENTS

| EP | 267986 A | 5/1988 |
| EP | 275312 A | 7/1988 |
| EP | 248523 B1 | 10/1991 |
| EP | 1205478 A | 5/2002 |
| EP | 1044970 | 1/2003 |
| EP | 1070708 A1 | 1/2004 |
| WO | WO 96/03392 A1 | 2/1996 |
| WO | WO 97/05131 A | 2/1997 |
| WO | WO 98/15543 A | 4/1998 |
| WO | WO 98/28282 A2 | 7/1998 |
| WO | WO 99/21555 A2 | 5/1999 |
| WO | WO 01/44207 A2 | 6/2001 |
| WO | WO 01/64674 A | 9/2001 |
| WO | WO 01/74793 A | 10/2001 |
| WO | WO 02/24200 A | 3/2002 |
| WO | WO 02/42298 A | 5/2002 |
| WO | WO 02/057240 | 7/2002 |
| WO | WO 03/015773 A | 2/2003 |
| WO | WO 03/062215 A | 7/2003 |
| WO | WO 03/094831 | 11/2003 |
| WO | WO 2004/096225 A | 11/2004 |
| WO | WO 2004/110350 A | 12/2004 |
| WO | WO 2005/012263 A1 | 2/2005 |
| WO | WO 2005/051917 A1 | 6/2005 |
| WO | WO 2005/070926 A | 8/2005 |
| WO | WO 2006/047256 | 5/2006 |
| WO | WO 2006/064375 A2 | 6/2006 |
| WO | WO 2007/031440 | 3/2007 |
| WO | 2007/118903 * | 10/2007 |
| WO | WO 2009/127678 A1 | 10/2009 |
| WO | WO 2012/113850 | 8/2012 |

OTHER PUBLICATIONS

Vippagunta et al., "Crystalline Solid", Advanced Drug Delivery Reviews 48 (2001) 3-26.*

(Continued)

*Primary Examiner* — Patricia Morris
(74) *Attorney, Agent, or Firm* — Hal B. Woodrow

(57) ABSTRACT

The present invention relates to substituted 1-(alkyl)-3-aniline-5-aryl triazole derivatives and analogues or pharmaceutically acceptable salts thereof, processes for preparing them, pharmaceutical compositions containing them and their use in therapy, according to Formula (I).

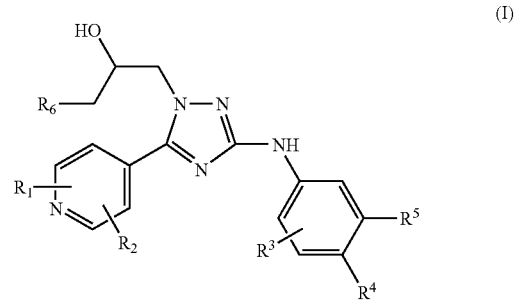

(I)

The invention particularly relates to potent positive allosteric modulators of nicotinic acetylcholine receptors which have the capability of increasing the efficacy of nicotinic receptor agonists.

8 Claims, No Drawings

OTHER PUBLICATIONS

Guillory (in Brittain ed.), "Polymorphism, etc.," NY: Marcel Dekker, Inc., 1999, 1-2, 125-181, 183-226.*

Yu et al., "Physical characterization of, etc.," PSTT, vl. 1(3), 118-127 (1998).*

Chen et al., in Bioorganic & Medicinal Chemistry Letters 11 (2001) 3165-3168.

Makara G.M., et al. (Organic Letters (2002) vol. 4 (10); 1751-1754.

International Search Report for PCT/EP2008/063845 dated Jan. 21, 2009.

Banerjee, Carolin et al., "Cellular Expression of α7 Nicotinic Acetylcholine Receptor Protein in the emporal Cortex in Alzheimer's and Parkinson's Disease—A Stereological Approach", Neurobiology of Disease, (2000), pp. 666-672, vol. 7.

Bickford, Paula C. et al., "Restoration of sensory gating of auditory evoked response by nicotine in fimbria-fornix lesioned rats", Brain Research, (1995), pp. 235-240, vol. 705.

Brown, D.J. et al., "The Chemistry of heterocyclic compounds: Fused Pyrimidines", Book—The Chemistry of Heterocyclic compounds, (1971), pp. 261-304, Chapter IV.

Burghaus, Lothar et al., "Quantitative assessment of nicotinic acetylcholine receptor proteins in the cerebral cortex of Alzheimer patients", Molecular Brain Research, (2000), pp. 385-388, vol. 76.

Dalack, Gregory W. et al., "Nicotine Dependence in Schizophrenia: Clinical Phenomena and Laboratory Findings", Am J Psychiatry, Nov. 1998, pp. 1490-1500, vol. 155:11.

Dani, John A. et al., "Variations in desensitization of nicotinic acetylcholine receptors from hippocampus and midbrain dopamine areas", European Journal of Pharmacology, (2000), pp. 1-38, vol. 393.

Freedman, Robert et al., "Evidence in Postmortem Brain Tissue for Decreased Numbers of Hippocampal Nicotinic Receptors in Schizophrenia", Biol Psychiatry, (1995), pp. 22-33, vol. 38.

Freedman, Robert et al., "Linkage of a neurophysiological deficit in schizophrenia to a chromosome 15 locus", Proc. Natl. Acad. Sci. USA, Jan. 1997, pp. 587-592, V. 94.

Gol'din et. al.. Hcaplus Abstract 1974:437516, "Synthesis of triazolones and C-aminotriazoles by the thermal condensation of carbamidoamidrazones", 1974.

Griffith, Jay M. et al., "Nicotinic Receptor Desensitization and Sensory Gating Deficits in Schizophrenia", Biol Psychiatry, 1998, pp. 98-106, vol. 44.

Guan, Zhi-Zhong et al., "Decreased protein level of nicotinic receptor α7 subunit in the frontal cortex from schizophrenic brain", NeuroReport, Jun. 3, 1999, pp. 1779-1782, vol. 10 No. 8.

Hamill, O. P. et al., "Improved Patch-Clamp Techniques for High-Resolution Current Recording from Cells and Cell-Free Membrane Patches", Pflugers Arch, (1981) pp. 85-100, vol. 391.

Intelihealth, "Alzheimer's disease," online, accessed Jun. 30, 2008, http://www.intelihealth.com/IH/intlhIWSIHWOOO/8303/9117/195703.html?d=dmtHealthAZ.

Intelihealth, "Dementia," online, accessed Sep. 22, 2009, http://www.intelihealth.com/IH/ihtIHIWSIHWOOO/24479/11184.html.

Intelihealth, "Parkinson's disease," online, accessed Sep. 22, 2009, http://www.intelihealth.com/IH/ihtIH?d=dmtHealthAZ&c=201957.

Intelihealth, "Schizophrenia" online, accessed Oct. 4, 2011, http://www.intelihealth.com/IH/ihtIHIWSIHWOOO/8271 /8694/1 8801 O.html?d=dmtHealthAZ#prevent.

Leonard, Sherry et al., "Association of Promoter Variants in the α7 Nicotinic Acetylcholine Receptor Subunit Gene With an Inhibitory Deficit Found in Schizophrenia", Arch Gen Psychiatry, Dec. 2002, pp. 1085-1096, vol. 59.

Lin et. al., "Recent developments in neuronal nicotinic acetycholine receptor modulators", 1998, 8 (8), pp. 991-1015.

Marutle, Amelia et al., "Laminar distribution of nicotinic receptor subtypes in cortical regions in schizophrenia", Journal of Chemical Neuroanatomy, (2001), pp. 115-126, vol. 22.

Muccioli, et al., "Latest Advances in Cannadinoid Receptor Antagonists and Inverse Agonists", Expert Opinion on Therapeutic Patents, vol. 16, No. 10, pp. 1405-1423, (2006).

Nagamatsu, Tomohisa et al., "General syntheses of—alkyltoxoflavin and 8-alkylfervenulin derivatives of biological significance by the regioselective alkylation of reumycin derivatives and the rates of transalkylation from 1-alkyltoxoflavins into nucleophiles", J. Chem. Soc., Perkin Trans., 2001, pp. 130-137.

Nagamatsu, Tomohisa et al., "Syntheses of 3-Substituted 1-Methyl-6-phenylpyrimido[5,4-e]-1,2,4-triazine-5,7(1H,6H)-diones (6-Phenyl Analogs of Toxoflavin) and Their 4-Oxides, and Evaluation of Antimicrobial Activity of Toxoflavins and Their Analogs", Chem. Pharm. Bull., (1993) pp. 362-368, vol. 41(2).

Ray, M.A. et al., "Neuronal nicotinic acetylcholine receptor subunits in autism: An immunohistochemical investigation in the thalamus", Neurobiology of Disease, (2005), pp. 366-377, vol. 19.

Ridley, Diana L. et al., "Differential effects of chronic drug treatment on α3* and α7 nicotinic receptor binding sites, in hippocampal neurons and SH-SY5Y cells", British Journal of Pharmacology , (2001), pp. 1286-1295, vol. 133.

Silverman, R. "The Organic Chemistry of Drug Design and Drug Action," 2004, Elsevier, pp. 29-32.

Stetter, Hermann et al., The Catalyzed Nucleophilic Addition of Aldehydes to Electrophilic Double Bonds*, Organic Reactions, (1991), pp. 407-496, vol. 40, Chapter 4.

Virginio, Caterina et al., "Pharmacological properties of rat α7 nicotinic receptors expressed in native and recombinant cell systems", European Journal of Pharmacology, (2002), pp. 153-161, vol. 445.

West, Anthony R., Solid State Chemistry and its Applications, Wiley, New York, 1988, pp. 358 & 365.

U.S. Appl. No. 13/512,464, Macdonald et al.

Office Action mailed Aug. 12, 2011 in U.S. Appl. No. 12/063,689.

Office Action mailed Dec. 21, 2011 in U.S. Appl. No. 12/063,689.

Final Office Action mailed Apr. 5, 2012 in U.S. Appl. No. 12/063,689.

Office Action mailed Dec. 2, 2011 in U.S. Appl. No. 12/738,725.

Notice of Allowance mailed Apr. 14, 2012 in U.S. Appl. No. 12/738,725.

Notice of Allowance mailed Jul. 19, 2012 in U.S. Appl. No. 12/738,725.

Office Action mailed May 2, 2012 in U.S. Appl. No. 12/866,054.

Office Action mailed Mar. 15, 2012 in U.S. Appl. No. 12/991,119.

Office Action mailed Jun. 22, 2012 in U.S. Appl. No. 12/991,119.

Notice of Allowance mailed Jul. 23, 2012 in U.S. Appl. No. 12/063,689.

Office Action mailed Aug. 10, 2012 in U.S. Appl. No. 12/866,054.

* cited by examiner

TRISUBSTITUTED 1,2,4 TRIAZOLES

CROSS REFERENCE TO RELATED APPLICATIONS

This application is the national stage of PCT Application No. PCT/EP2008/063845, filed Oct. 15, 2008, which claims priority from European Patent Application No. 07118825.4, filed Oct. 18, 2007, the entire disclosures of which are hereby incorporated in their entirety.

The present invention relates to substituted 1-alkyl-3-aniline-5-aryl triazole derivatives and pharmaceutically acceptable salts thereof, processes for preparing them, pharmaceutical compositions containing them and their use in therapy. The invention relates to selective, potent positive allosteric modulators of α7 nicotinic acetylcholine receptors which have the capability of increasing the efficacy of nicotinic receptor agonists.

BACKGROUND PRIOR ART

EP 1044970 describes 3-alkylamino-1,2,4-triazoles as neuropeptide Y receptor ligands.

The paper by Makara G. M., et al. (Organic Letters (2002) Vol. 4 (10); 1751-1754) describes the solid-phase synthesis of 3-alkylamino-1,2,4-triazoles and exemplifies the unsuccessful synthesis of N-(4-methoxyphenyl)-1-methyl-5 (4-methylphenyl)-1H-1,2,4-triazol-3-amine and is silent about potential therapeutic applications of this compound, in particular about its use as a positive allosteric modulator of the α7 nicotinic acetylcholine receptor.

Chen Chen et al., in Bioorganic & Medicinal Chemistry Letters 11 (2001) 3165-3168 describes the synthesis of 1-alkyl-3-amino-5-aryl-1H-[1,2,4]triazoles, in particular N-(2-methoxyphenyl)-1-methyl-5-(2,4-dichlorophenyl)-1H-1,2,4-triazol-3-amine, and their use as corticotropin-releasing factor-1 (CRF1) antagonists.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called β subunits, and a second group containing α subunits. Three kinds of α subunits, α7, α8 and α9, have been shown to form functional receptors when expressed alone and thus are presumed to form homooligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors have been implicated in a number of diseases. Some of these, for example myasthenia gravis and autosomal dominant nocturnal front lobe epilepsy (ADNFLE) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors and since the effect of nicotine is to stabilize receptors in a desensitized state, an increased activity of nicotinic receptors may reduce the desire to smoke.

Compounds which bind nAChRs have been suggested for the treatment of a range of disorders involving reduced cholinergic function such as learning deficit, cognition deficit, attention deficit or memory loss. Modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to reduce activity as well as enhance it.

At nicotinic receptors in general, and particularly at the α7-nicotinic receptor, desensitization limits the duration of action of an applied agonist.

DESCRIPTION OF THE INVENTION

We have surprisingly found that certain novel compounds can increase the efficacy of agonists at nicotinic acetylcholine receptors. Compounds having this type of action are referred to as "positive allosteric modulators" and are likely useful for treatment of conditions associated with reductions in nicotinic transmission. In a therapeutic setting such compounds could restore normal interneuronal communication without affecting the temporal profile of activation. In addition, positive allosteric modulators are not expected to produce long-term inactivation of receptors as may occur after repeated or prolonged application of agonists.

The positive nAChR modulators of the present invention are useful for treatment or prophylaxis of psychotic disorders, intellectual impairment disorders or diseases, or inflammatory diseases or conditions in which modulation of the α7 nicotinic receptor is beneficial.

The present invention concerns substituted 1-alkyl-3-aniline-5-aryl triazole derivatives having positive allosteric modulator properties, increasing the efficacy of agonists at the α7 nicotinic receptor. The invention further relates to methods for their preparation and pharmaceutical compositions comprising them. The invention also relates to compounds according to formula (I) for use in the treatment or prevention of psychotic disorders, intellectual impairment disorders or diseases, inflammatory diseases or conditions in which modulation of the α7 nicotinic receptor is beneficial. The invention also relates to the use of these derivatives for the manufacture of a medicament for the treatment or prophylaxis of psychotic disorders, intellectual impairment disorders or diseases, inflammatory diseases or conditions in which modulation of the α7 nicotinic receptor is beneficial.

The compounds of the present invention differ structurally from the prior art compounds and pharmacologically by their activity as positive allosteric modulators of the α7 nicotinic acetylcholine receptor. The absolute configuration at the chiral carbon atom has a subtle effect on the electrophysiological response of the α7 nicotinic acetylcholine receptor.

The present invention relates to a compound according to formula (I)

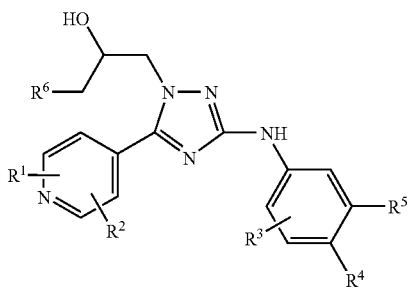

(I)

or a stereoisomeric form thereof, wherein
$R^1$ is methyl, ethylamino or methoxyethylamino;
$R^2$ is hydrogen or methyl;
$R^3$ is fluoro, chloro, trifluoromethyl or methyl;
$R^4$ is hydrogen or fluoro;
$R^5$ is hydrogen, fluoro, chloro or methoxy;
$R^6$ is $C_{1-3}$alkyl;
or a pharmaceutically acceptable salt or a hydrate or a solvate thereof.

In a first embodiment the present invention relates to a compound according to formula (I-a)

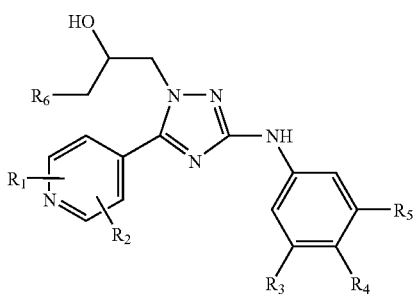

(I-a)

or a stereoisomeric form thereof, $R^1$ is methyl, ethylamino or methoxyethylamino;
$R^2$ is hydrogen or methyl;
$R^3$ is fluoro, chloro, trifluoromethyl or methyl;
$R^4$ is hydrogen or fluoro;
$R^5$ is hydrogen, fluoro, chloro or methoxy;
$R^6$ is $C_{1-3}$alkyl;
or a pharmaceutically acceptable salt or a hydrate or a solvate thereof.

In a second embodiment the present invention relates to a compound according to formula (I-a)

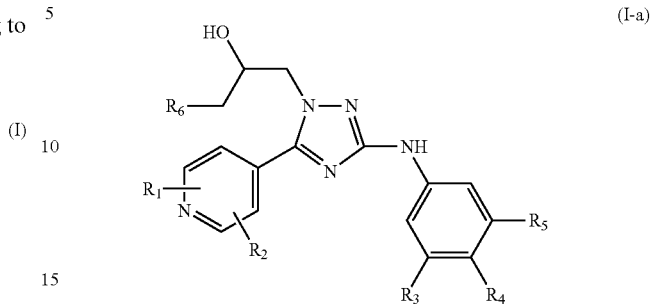

(I-a)

or a stereoisomeric form thereof, wherein
$R^1$ is methyl, ethylamino or methoxyethylamino;
$R^2$ is hydrogen or methyl;
$R^3$ is fluoro, chloro, trifluoromethyl or methyl;
$R^4$ is hydrogen or fluoro;
$R^5$ is hydrogen, fluoro or methoxy;
$R^6$ is $C_{1-3}$alkyl;
or a pharmaceutically acceptable salt or a hydrate or a solvate thereof.

In a third embodiment the present invention relates to a compound according to formula (I) or a stereoisomeric form thereof, wherein
$R^1$ is 2-methyl, 2-ethylamino or 2-methoxyethylamino;
$R^2$ is hydrogen or 6-methyl;
$R^3$ is fluoro, chloro, trifluoromethyl or methyl;
$R^4$ is hydrogen or fluoro;
$R^5$ is hydrogen, fluoro, chloro or methoxy;
$R^6$ is $C_{1-3}$alkyl;
or a pharmaceutically acceptable salt or a hydrate or a solvate thereof.

In a fourth embodiment the present invention relates to a compound according to formula (I) or a stereoisomeric form thereof, wherein
$R^1$ is 2-methyl, 2-ethylamino or 2-methoxyethylamino;
$R^2$ is hydrogen or 6-methyl;
$R^3$ is fluoro, chloro, trifluoromethyl or methyl;
$R^4$ is hydrogen or fluoro;
$R^5$ is hydrogen, fluoro, chloro or methoxy;
$R^6$ is methyl;
or a pharmaceutically acceptable salt or a hydrate or a solvate thereof.

In a fifth embodiment, the present invention relates to a compound according to formula (I) having the absolute R-configuration.

In a sixth embodiment, the present invention relates to a compound according to formula (I) having the absolute S-configuration.

In a seventh embodiment, the present invention relates to a compound according to formula (I) having the $R^3$ substitution in the ortho position of the phenyl ring.

In an eighth embodiment, the present invention relates to a compound according to any of the previous embodiments, wherein
$R^5$ is hydrogen, fluoro or methoxy.

In a ninth embodiment the compound of Formula (I) is selected from the group comprising:
(S)-1-[3-(3,4-difluoro-phenylamino)-5-(2,6-dimethyl-pyridin-4-yl)-[1,2,4]triazol-1-yl]-butan-2-ol, (R)-1-[3-(3-chloro-phenylamino)-5-(2-ethylamino-pyridin-4-yl)-[1,2,4]triazol-1-yl]-butan-2-ol,
(S)-1-[5-(2,6-Dimethyl-pyridin-4-yl)-3-(3-methoxy-5-trifluoromethyl-phenylamino)-[1,2,4]triazol-1-yl]-butan-2-ol,
(S)-1-[3-(3-Fluoro-5-methoxy-phenylamino)-5-(2-methyl-pyridin-4-yl)-[1,2,4]triazol-1-yl]-butan-2-ol HCl salt,
(S)-1-[3-(3-Fluoro-5-methoxy-phenylamino)-5-(2-methyl-pyridin-4-yl)-[1,2,4]triazol-1-yl]-butan-2-ol,
(S)-1-[5-(2,6-Dimethyl-pyridin-4-yl)-3-(3-fluoro-5-methoxy-phenylamino)-[1,2,4]triazol-1-yl]-butan-2-ol HCl salt,
(S)-1-[5-(2,6-Dimethyl-pyridin-4-yl)-3-(3-fluoro-5-methoxy-phenylamino)-[1,2,4]triazol-1-yl]-butan-2-ol,
(S)-1-[3-(4-Fluoro-3-methyl-phenylamino)-5-(2-methyl-pyridin-4-yl)-[1,2,4]triazol-1-yl]-butan-2-ol,
including any stereochemically isomeric form thereof,
and the pharmaceutically acceptable addition salts and the solvates thereof.

In a tenth embodiment the compound of Formula (I) is selected from the group comprising:
(S)-1-[5-(2-Methyl-pyridin-4-yl)-3-(2,3,4-trifluoro-phenylamino)-[1,2,4]triazol-1-yl]-butan-2-ol,
(S)-1-[5-(2,6-Dimethyl-pyridin-4-yl)-3-(2,3,4-trifluoro-phenylamino)-[1,2,4]triazol-1-yl]-butan-2-ol,
(S)-1-[5-(2,6-Dimethyl-pyridin-4-yl)-3-(2,3,4-trifluoro-phenylamino)-[1,2,4]triazol-1-yl]-butan-2-ol HCl salt,
(S)-1-[3-(3-Chloro-2-fluoro-phenylamino)-5-(2,6-dimethyl-pyridin-4-yl)-[1,2,4]triazol-1-yl]-butan-2-ol,
(S)-1-[3-(3-Chloro-2-fluoro-phenylamino)-5-(2,6-dimethyl-pyridin-4-yl)-[1,2,4]triazol-1-yl]-butan-2-ol HCl salt,
including any stereochemically isomeric form thereof,
and the pharmaceutically acceptable addition salts and the solvates thereof.

In a further embodiment, the present invention preferably relates to (S)-1-[3-(3,4-difluoro-phenylamino)-5-(2,6-dimethyl-pyridin-4-yl)-[1,2,4]triazol-1-yl]-butan-2-ol, or (R)-1-[3-(3-chloro-phenylamino)-5-(2-ethylamino-pyridin-4-yl)-[1,2,4]triazol-1-yl]-butan-2-ol.

The compounds according to formula (I) and their addition salts, hydrates and solvates, contain one or more centers of chirality and exist as stereochemically isomeric forms.

The term "stereochemically isomeric forms" as used hereinbefore or hereinafter defines all the possible stereoisomeric forms which the compounds according to formula (I) and their addition salts may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their salts, solvates, substantially free, i.e. associated with less than 10%, preferably less than 5%, in particular less than 2% and most preferably less than 1% of the other isomers. Stereochemically isomeric forms of the compounds according to formula (I) are obviously intended to be embraced within the scope of this invention.

For therapeutic use, salts of the compounds according to formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds according to formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The term solvates refers to hydrates and alcoholates which the compounds according to formula (I) as well as the salts thereof, may form.

Some of the compounds according to formula (I) may also exist in their tautomeric form. Such forms although not explicitly indicated in the above formula are intended to be included within the scope of the present invention.

Preparation of the Compounds

A compound according to the invention can generally be prepared by a succession of steps, each of which is known to the skilled person. In particular, the compounds in this patent application can be prepared according to one or more of the following preparation methods. In the following schemes, and unless otherwise indicated, all variables are used as defined in Formula (I). L' represents a radical of formula

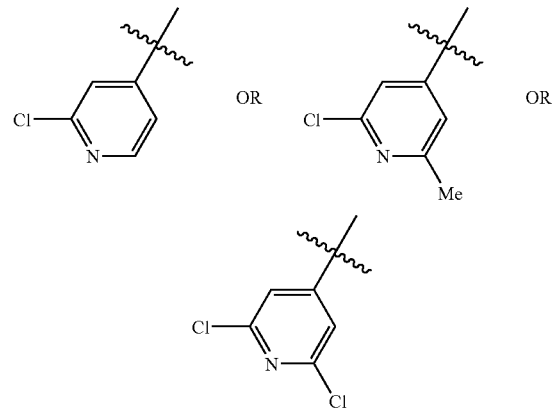

and Q represents

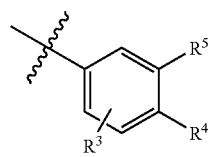

wherein $R^3$, $R^4$ and $R^5$ are as defined hereinbefore.

The compounds of this invention can be prepared by any of several standard synthetic processes commonly used by those skilled in the art of organic chemistry.

Scheme 1

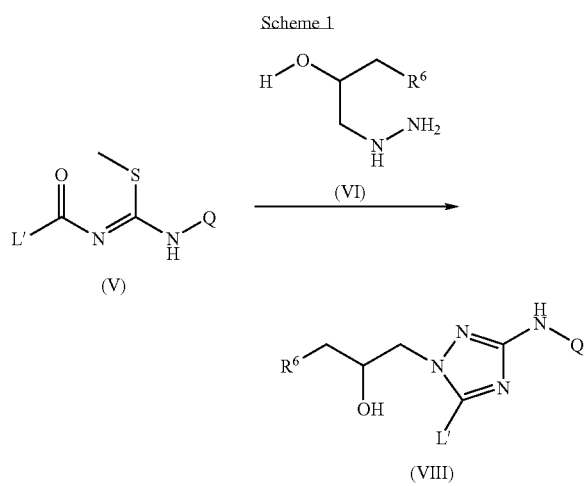

Crucial intermediates according to formula (VIII), can generally be prepared according to Scheme 1 by transforming an N-acyl carbonimidothioic acid, methyl ester derivative of general formula (V) into the 1,2,4-triazoles of formula (VIII) using an appropriate hydrazine (VI) under art known conditions. This transformation is typically performed in a protic solvent, such as methanol or a higher alcohol such as, for example, 2-methyl-2-propanol (t-BuOH) and requires a temperature between room temperature and 150° C. In a particular embodiment the higher alcohol is tertiary butyl alcohol and the reaction temperature is between 70° and 120° C., most preferably 100° C. For those reactions wherein the hydrazine (VI) is used as an HCl salt, the addition of a stoichiometric amount of a base is preferred. Said base can be an inorganic base, such as potassium acetate or potassium carbonate, more preferably however, said base is a tertiary amine, such as diisopropyl ethyl amine or the like (Scheme 1). All variables in Scheme 1 are as defined before.

Optionally, the free hydroxyl group in intermediates of formula (VIII) can be protected by a typical protecting group (PG), hereby named (VIII-1), such as, for example, an acetyl group. This type of reaction may be performed in the presence of ethyl acetate. Typically a catalyst such as, for example, N,N-dimethyl-4-pyridinamine (DMAP), is added. The reaction can be performed at an elevated temperature such as, for example, at reflux temperature.

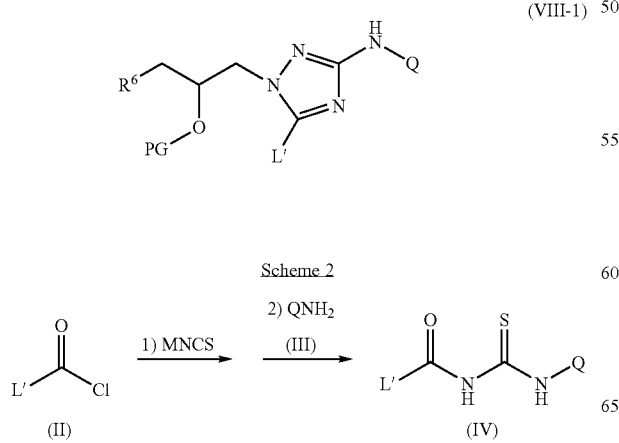

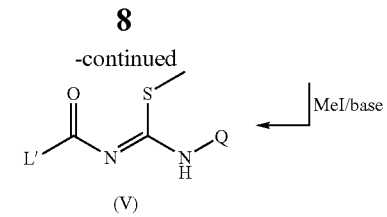

The common intermediate (V) in the synthesis of the trisubstituted triazoles of the present invention is typically prepared by a protocol that consists of 3 synthetic transformations (Scheme 2), starting from an acyl chloride of the general formula (II). In a first step an acylating agent, such as an acyl chloride (II), a mixed or symmetric anhydride, an acyl fluoride or the like; is reacted with a monovalent cation ($M^+$) thiocyanate (MNCS in scheme 2), such as for example potassium thiocyanate or ammonium thiocyanate to yield the corresponding acyl isothiocyanate. This reaction is usually performed using acetone as a solvent and at a temperature between 0° C. and 70° C., preferably at room temperature.

The intermediate acyl isothiocyanate is not isolated but treated in the same reaction medium with an appropriate aniline (III) to yield the N-acyl thiourea of the general formula (IV). This transformation is usually performed at a temperature between 0° C. and 70° C., preferably at room temperature.

In a final step, S-methylation of the N-acyl thiourea (IV) provides the N-acyl carbonimidothioic acid, methyl ester derivative of general formula (V). This final transformation requires the presence of a base, preferably a strong inorganic base, such as NaH or potassium carbonate, and is performed in an aprotic solvent such as for example DMF, THF (tetrahydrofuran) or the like, at a temperature ranging from −70° C. to room temperature, preferably 0° C. (Scheme 2).

Scheme 3

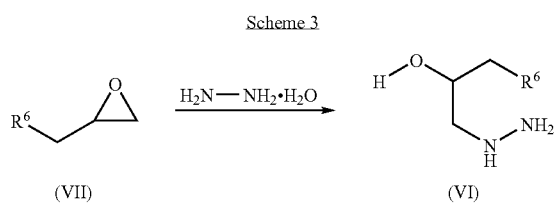

The hydrazine alcohols of the general formula VI can be prepared from a mono-substituted oxirane of the general formula (VII) by heating in an excess of hydrazine hydrate (Scheme 3). Preferably the reaction temperature is 40-70° C. and the reaction time 2 hours. If the oxirane (VII) is available in optically pure form, the resulting hydrazine alcohol (VI) is obtained with the corresponding stereochemical identity and purity, such as for example when $R^6$=methyl. In other examples in the present invention, said oxirane (VII) is available as a racemic mixture, and hence the corresponding intermediates and final products are obtained as racemic mixtures. In such a case, the final products can be obtained in enantiomerically pure form by separation of the racemic mixture using chiral chromatography. In a particular embodiment said chiral chromatography is performed with supercritical $CO_2$ as the mobile phase.

Scheme 4

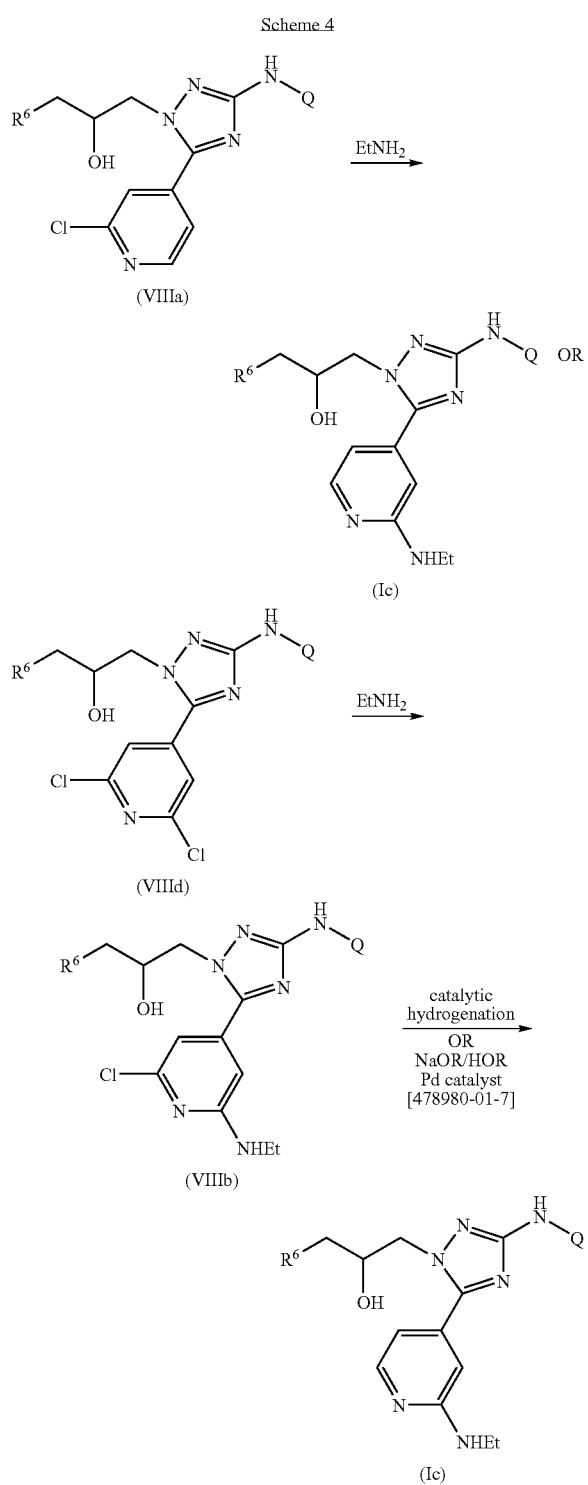

between 100° C. and 130° C.) by starting from the dichloro pyridyl compound (VIIId) to afford the intermediate of the general formula (VIIIb). The remaining chlorine atom in (VIIIb) can be removed catalytically, under a hydrogen atmosphere and using Pd/C as the catalyst, in the presence of an inorganic base, such as potassium acetate, or an amine base, such as triethyl amine, or the like (Scheme 4). Alternatively, when the substituent Q contains functionalities that are not compatible with catalytic hydrogenation conditions, the target compound of the general formula (Ic) can be obtained from the chloro pyridine of the general formula (VIIIb), by treatment with a carbenoid catalyst, such as the Pd catalyst [1,3-bis[2,6-bis(1-methylethyl)phenyl]-2-imidazolidinylidene]chloro(η3-2-propenyl)-palladium (CAS [478980-01-7]), in the presence of a strong base, such as sodium methoxide in a protic solvent, such as methanol or 2-propanol, or the like. Said reaction can be carried out at elevated temperature, such as 100-120° C. in a microwave oven (Scheme 4).

Scheme 5

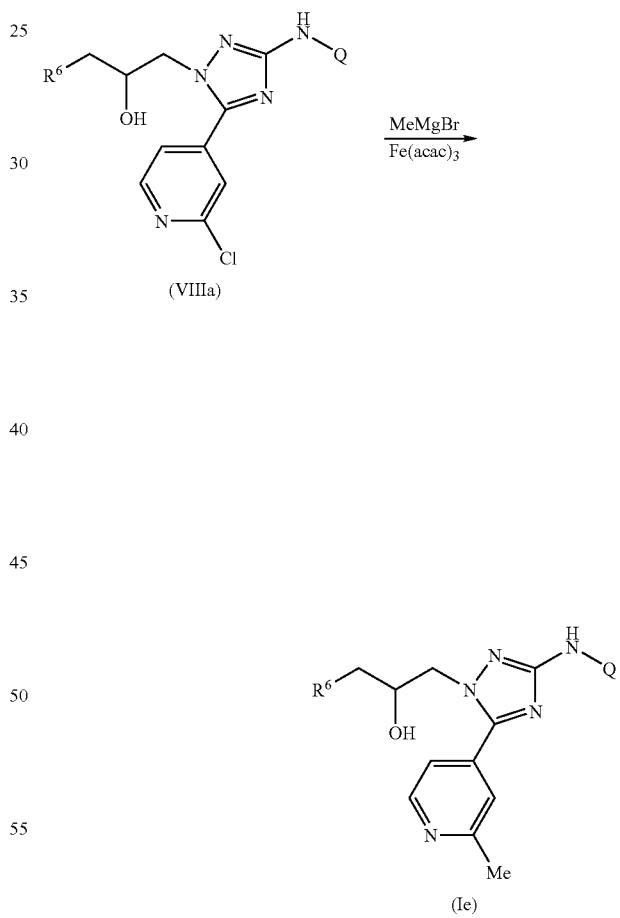

The 2-ethylamino-pyrido triazole of the general formula (Ic) can be obtained by treatment of the corresponding chloro pyridyl precursor (VIIIa) with ethyl amine in an alcoholic solvent, such as methanol or 1-butanol or the like, optionally in the presence of a co-solvent such as THF or the like, and heating at high temperatures, preferably in a range between 140° C. and 160° C. in a microwave oven, or at 160° C.-180° C. in an autoclave (Scheme 4). Said transformation can be effected under milder conditions (lower temperature, such as A mono-methyl-substituted pyrido triazole of the general formula (Ie), can be prepared by treatment of the 2-chloro pyridyl precursor (VIIIa) with an excess (3-15 equiv.) Grignard reagent MeMgBr in the presence of a catalytic amount of Iron(III)acetylacetonate in an organic solvent or a solvent system consisting of different solvents such as, for example, a mixture of THF/NMP. Typical THF/NMP (1-methyl-2-pyrrolidinone) mixtures consist of 75% to 99% THF and 1% to 25% NMP by volume. Said transformation can be performed in a temperature range between 0° C. and 50° C., most preferably between 0° C. and 25° C. (Scheme 5).

Scheme 6

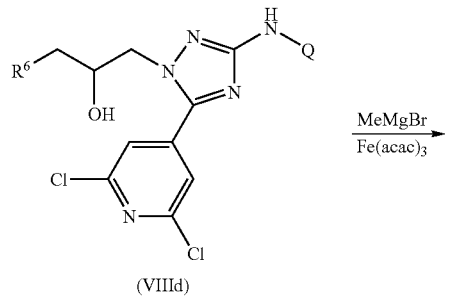

(VIIId)

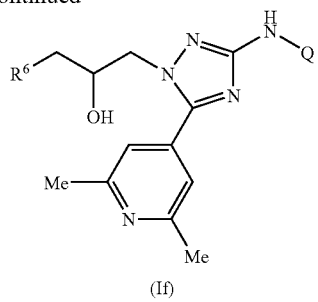

(If)

A di-methyl-substituted pyrido triazole of the general formula (If), can be prepared by treatment of the 2,6-dichloro pyridyl precursor (VIIId) with an excess (10-15 equiv.) Grignard reagent MeMgBr in the presence of a catalytic amount of Iron(III)acetylacetonate in an organic solvent or a solvent system consisting of different solvents such as, for example, a mixture of THF/NMP. Typical THF/NMP (1-methyl-2-pyrrolidinone) mixtures consist of 75% to 99% THF and 1% to 25% NMP by volume. Said transformation can be performed in a temperature range between 0° C. and 50° C., most preferably between 0° C. and 25° C. (Scheme 6).

Scheme 7

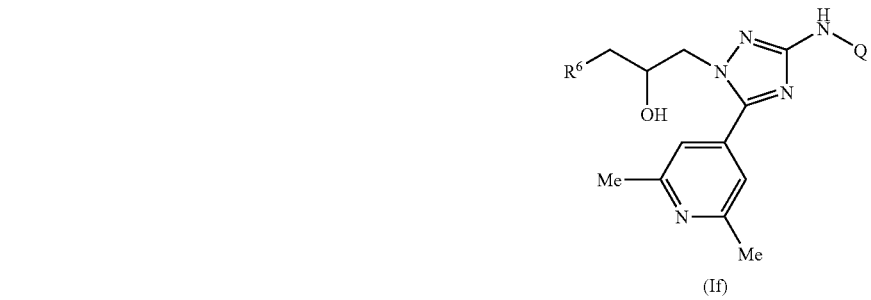

(If)

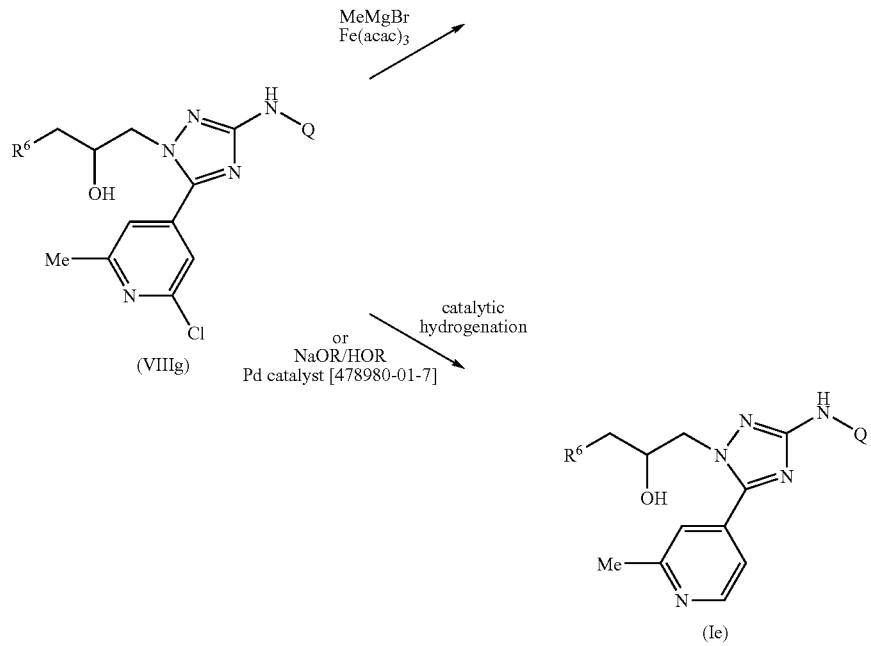

(Ie)

Alternatively, the mono-methyl-substituted pyrido triazole of the general formula (Ie) and the di-methyl-substituted pyrido triazole of the general formula (If) can be obtained through a common intermediate (VIIIg) (Scheme 7). Reaction with a methyl Grignard reagent MeMgBr, catalyzed by Iron(III)acetylacetonate, using conditions as described above, leads to the final compound (If) (Scheme 7). Upon catalytic hydrogenation of intermediate (VIIIg) using art-known conditions as described above, the final compound (Ie) is formed. Alternatively, when the substituent Q contains functionalities that are not compatible with catalytic hydrogenation conditions, the target compound of the general formula (Ie) can be obtained from the chloro pyridine of the general formula (VIIIg), by treatment with a carbenoid catalyst, such as the Pd catalyst [1,3-bis[2,6-bis(1-methylethyl)phenyl]-2-imidazolidinylidene]chloro(η3-2-propenyl)-palladium (CAS [478980-01-7]), in the presence of a strong base, such as sodium methoxide in a protic solvent, such as methanol or 2-propanol, or the like. Said reaction can be carried out at elevated temperature, such as 100-120° C. in a microwave oven.

In case the intermediate (VIIIg) has a protected hydroxyl group such as, for example, an acetate, a compound of the general formula (If) can be obtained by reaction with a methyl Grignard reagent MeMgBr, catalyzed by Iron(III)acetylacetonate in the presence of an organic solvent or a mixture of organic solvents such as, for example, a mixture of NMP and THF. To facilitate the removal of the protecting group (such as for example the acetyl group) optionally a base such as, for example, NaOH may be added to the reaction mixture.

Pharmacology

The compounds of the present invention were found to be positive allosteric modulators of the α7 nicotinic receptor. The α7 nicotinic receptor (α7 nAChR) belongs to the super-family of cys-loop, ionotropic ligand-gated ion channels which includes the 5-HT$_3$, GABA$_A$ and glycine receptor families. It is activated by acetylcholine and its breakdown product choline and a major feature of the α7 nAChR is its rapid desensitisation in the persistent presence of agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans. It is also implicated in the cholinergic inflammatory pathway.

Genetic evidence for its association with schizophrenia is seen in the form of strong linkage between a schizophrenia marker (sensory gating deficit) and the α7 locus on 15q13-14 and polymorphisms in core promoter region of the α7 gene.

Pathological evidence points to a loss of α7 immunoreactivity and α-Btx-binding in the hippocampus, frontal and cingulate cortex of schizophrenic brains, in Parkinson's and Alzheimer's disease and paraventricular nucleus and nucleus reuniens in autism.

Pharmacological evidence such as the marked smoking habits of schizophrenics compared to normals have been interpreted as an attempt by the patients to self-medicate to make up for a deficit in α7 nicotinergic transmission. Transient normalization of defects in sensory gating (pre-pulse inhibition PPI) in both animal models and man upon nicotine administration and temporary restoration of normal sensory gating in schizophrenics when forebrain cholinergic activity low (e.g. stage 2 sleep) have both been interpreted to be the result of transient activation of the α7 nicotinic receptor followed by desensitisation.

Thus there is good reason to suppose that activating the α7 nAChR will have therapeutically beneficial effects for a number of CNS (psychiatric and neurological) disorders.

As already mentioned the α7 nAChR rapidly desensitizes in the persistent presence of the natural transmitter acetylcholine as well as exogenous ligands such as nicotine. In the desensitized state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatible and desensitized α7 nAChRs in a physiologically useful range. However, synthetic agonists, which are not substrates for the natural breakdown and clearance mechanisms are perceived to have a potential liability both for over-stimulation and also to push the α7 nAChR population equilibrium towards a persistently desensitized state, which is undesirable in disorders in which deficiencies in α7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to α7 agonism is to enhance receptor responsiveness to the natural agonists with a positive allosteric modulator (PAM). A PAM is defined as an agent which binds to a site distinct from the agonist binding site, and therefore is not expected to have agonist or desensitization properties, but enhances the responsiveness of the α7 nAChR to the natural transmitter. The value of this strategy is that for a given amount of transmitter the magnitude of α7 nAChR response is increased in the presence of the PAM relative to the level of transmission possible in its absence. So for disorders in which there is a deficit in α7 nAChR protein the PAM-induced increase in α7 nicotinergic transmission can be beneficial. As a PAM relies on the presence of the natural transmitter the potential for over-stimulation is limited by the breakdown/clearance mechanisms for the natural transmitter.

The compounds of the present invention are classified as type 1-4, based on qualitative kinetic properties, as determined by whole-cell voltage-clamp recordings. This classification is based on the effect of an α7 PAM compound, as described hereinbefore, on the signal elicited by an agonist application. In particular, said agonist is choline at a concentration of 1 mM. In a preferred experimental setting, said α7 PAM compound and choline are simultaneously applied to the cell, as described hereinafter. Desensitization is defined as the closure of the receptor upon activation during the application of the agonist in whole-cell voltage-clamp electrophysiology measurements seen as the reduction of the outward current after initial activation by the agonist.

The definition of the PAM types 1-4 is described hereinafter:

Type 1 compounds enhance the effect size of the current elicited by 1 mM choline but minimally alter the kinetics of the receptor. In particular, the rate and the extent of desensitization, elicited by the agonist, is not affected. The compound-modulated response to 1 mM choline, therefore, is a close to linear scaling of the 1 mM choline response in absence of the α7 PAM compound.

Type 2 compounds enhance the effect size of the current elicited by 1 mM choline while reducing the rate and/or the extent of desensitization.

Type 3 compounds enhance the effect size of the current elicited by 1 mM choline. When tested at higher concentrations up to 10 µM they completely inhibit desensitization, in particular a 1 mM choline application of 250 milliseconds.

Type 4 compounds allow for an initial desensitization of the receptor followed by a re-opening of the receptor during agonist application. At low-potency concentrations of the α7 PAM compound, the agonist-induced activation, which is followed by desensitization, can still be separated from the compound-induced re-opening as an initial inward current-maximum. At higher potency concentrations of the α7 PAM compound, the re-opening occurs faster than the closure due to desensitization so that the initial current-maximum disappears.

It is accordingly an object of the present invention to provide methods of treatment that include administering either a positive allosteric modulator as the only active substance, thus modulating the activity of endogenous nicotinic receptor agonists such as acetylcholine or choline, or administering a positive allosteric modulator together with a nicotinic receptor agonist. In a particular form of this aspect of the invention, the method of treatment comprises treatment with a positive allosteric modulator of the α7 nicotinic receptor as described herein and an α7 nicotinic receptor agonist or partial agonist. Examples of suitable compounds with α7 nicotinic receptor agonistic activity include, but are not limited to:

1,4-Diazabicyclo[3.2.2]nonane-4-carboxylic acid, 4-bromophenyl ester, monohydrochloride (SSR180711A);

(−)-spiro[1-azabicyclo[2.2.2.]octane-3,5'-oxazolidine]-2'-one;

3-[(2,4-Dimethoxy)Benzylidene]-Anabaseine Dihydrochloride (GTS-21);

[N-[(3R)-1-Azabicyclo[2.2.2]oct-3-yl]-4-chlorobenzamide Hydrochloride] PNU-282987).

Positive nAChR modulators of the present invention are useful for treatment or prophylaxis of psychotic disorders, intellectual impairment disorders or diseases or conditions in which modulation of α7 nicotinic receptor activity is beneficial. A particular aspect of the method of the invention is a method of treatment for learning deficit, cognition deficit, attention deficit or memory loss, modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

The compounds may also find therapeutical use as anti-inflammatory medicines because the nicotinic acetylcholine receptor α7 subunit is essential for inhibiting cytokine synthesis by the cholinergic inflammatory pathway. Examples of indications which may be treated by the compounds are endotoxaemia, endotoxic shock, sepsis, rheumatoid arthritis, asthma, multiple sclerosis, inflammatory bowel disease, inflammatory bile disease, Crohn's disease, pancreatitis, heart failure, and allograft rejection.

In view of the above described pharmacological properties, the compounds according to formula (I) or any subgroup thereof, their pharmaceutically acceptable addition salts and stereochemically isomeric forms, may be used as a medicament.

In view of the above described pharmacological properties, the compounds according to formula (I) or any subgroup thereof, their pharmaceutically acceptable addition salts and stereochemically isomeric forms, may be used in the treatment or prevention of psychotic disorders, intellectual impairment disorders or diseases, inflammatory diseases or conditions in which modulation of the α7 nicotinic receptor is beneficial.

In view of the above described pharmacological properties, the present compounds can be used for the manufacture of a medicament for treatment or prophylaxis of psychotic disorders, intellectual impairment disorders or diseases, inflammatory diseases or conditions in which modulation of the α7 nicotinic receptor is beneficial.

In view of the utility of the compounds according to formula (I), there is provided a method of treating warm-blooded animals, including humans, suffering from or a method of preventing warm-blooded animals, including humans, to suffer from diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said methods comprise the administration, i.e. the systemic or topical administration, preferably oral administration, of an effective amount of a compound according to formula (I), including all stereochemically isomeric forms thereof, a pharmaceutically acceptable addition salt, a solvate, or a hydrate thereof, to warm-blooded animals, including humans.

One skilled in the art will recognize that a therapeutically effective amount of the PAM's of the present invention is the amount sufficient to modulate the activity of the α7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 µM, and more usually 5 nM to 50 µM. To obtain these treatment concentrations, a patient in need of treatment likely will be administered between 0.005 mg/kg to 10 mg/kg body weight, in particular from 0.1 mg/kg to 0.50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds according to formula (I) may also be used in combination with other conventional α7 nicotinic receptor agonists, such as for example 1,4-Diazabicyclo[3.2.2]nonane-4-carboxylic acid, 4-bromophenyl ester, monohydrochloride (SSR180711A); (−)-spiro[1-azabicyclo[2.2.2.]octane-3,5'-oxazolidine]-2'-one; 3-[(2,4-Dimethoxy)Benzylidene]-Anabaseine Dihydrochloride (GTS-21); or [N-[(3R)-1-Azabicyclo[2.2.2]oct-3-yl]-4-chlorobenzamide Hydrochloride] PNU-282987). Thus, the present invention also relates to the combination of a compound according to formula (I) and a α7 nicotinic receptor agonist. Said combination may be used as a medicine. The present invention also relates to a product comprising (a) a compound according to formula (I), and (b) an α7 nicotinic receptor agonist, as a combined preparation for simultaneous, separate or sequential use in the treatment of diseases wherein modulation of the α7 nicotinic receptor is beneficial. The different drugs may be combined in a single preparation together with pharmaceutically acceptable carriers.

EXPERIMENTAL PART

Chemistry

Several methods for preparing the compounds of this invention are illustrated in the following Examples. Unless otherwise noted, all starting materials were obtained from commercial suppliers and used without further purification.

Hereinafter and hereinbefore, "THF" means tetrahydrofuran; "EtOAc" means ethyl acetate; "DIPE" means diisopropylether; "DMF" means N,N-dimethylformamide; "NMP" means 1-methyl-2-pyrrolidinone, "q.s." means quantum sufficit, "I.D." means internal diameter, and "t-BuOH" means 2-methyl-2-propanol.

Microwave assisted reactions were performed in a single-mode reactor: Initiator™ Sixty EXP microwave reactor

A. Preparation of the Intermediates

Description 1

1-(2-Chloro-6-methyl-pyridine-4-carbonyl)-3-(3,4-difluoro-phenyl)-thiourea (D1)

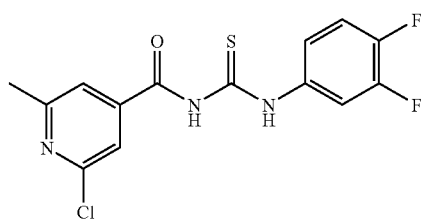 [SMILES: Cc1cc(C(=O)NC(=S)Nc2ccc(F)c(F)c2)cc(Cl)n1]

Thiocyanic acid ammonium salt (10.6 g) was added to a mixture of 2-chloro-6-methyl-4-pyridinecarbonyl chloride (22.04 g; 116 mmol) and acetone (400 ml). The reaction mixture was stirred for 30 minutes and then 3,4-difluorobenzenamine (14.98 g; 116 mmol) was added slowly via an additional funnel. The resulting solution was stirred for 2 hours, quenched by water (100 ml) and then extracted by $CH_2Cl_2$ (3×100 ml). The combined organic phase was dried over $MgSO_4$, filtered and the solvent was evaporated in vacuo. Yield: 38.1 g of intermediate D1.

Description 2

1-(2-Chloro-6-methyl-pyridine-4-carbonyl)-3-(3,4-difluoro-phenyl)-2-methyl-isothiourea (D2)

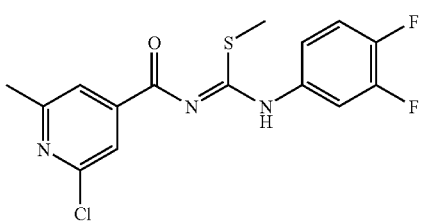 [SMILES: CS/C(=N\C(=O)c1cc(C)nc(Cl)c1)Nc1ccc(F)c(F)c1]

A mixture of intermediate D1 (38 g; 111.4 mmol) in THF (400 ml) was cooled to 0° C. and NaH (60% pure) (6.7 g; 167 mmol) was carefully added. The reaction mixture was stirred for 15 minutes and then $CH_3I$ (14.2 g; 100 mmol) was added. The mixture was then warmed to room temperature and stirred for 2 hours. The reaction was quenched by the addition of water and then the mixture was extracted by $CH_2Cl_2$ (3×100 ml). The combined organic solvent was washed with brine, dried over $MgSO_4$, filtered and the solvent was evaporated in vacuo. The residue was purified by silica column chromatography (gradient: Heptane/EtOAc from 80/20 to 50/50). Yield: 22.2 g of intermediate D2.

Description 3

(S)-1-Hydrazino-butan-2-ol (D3)

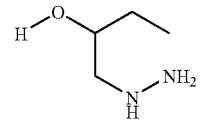

(2-S) 2-ethyloxirane (15 g; 208 mmol) was dissolved in hydrazine, 64% (42 g; 832 mmol). The reaction mixture was stirred at 50° C. for 2 hours and then evaporated under the hood in a water bath at 50° C. Xylene was added (×2) to co-evaporate the excess amount of hydrazine from the crude reaction mixture. Yield: 18.9 g of intermediate D3 (white solid; S-enantiomer).

Description 4

(S)-1-[5-(2-Chloro-6-methyl-pyridin-4-yl)-3-(3,4-difluoro-phenylamino)-[1,2,4]triazol-1-yl]-butan-2-ol (D4)

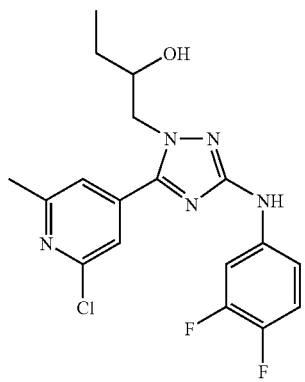 [SMILES: CCC(O)Cn1nc(Nc2ccc(F)c(F)c2)nc1-c1cc(C)nc(Cl)c1]

Intermediate D2 (1 g; 2.81 mmol) was dissolved in t-BuOH (40 ml) and, then intermediate D3 (0.44 g; 4.22 mmol) was added. The reaction mixture was stirred and refluxed for 4 hours and then the solvent was evaporated. The residue was purified by silica column chromatography (gradient: $CH_2Cl_2$/ 10% $CH_3OH$ in $CH_2Cl_2$ from 100/0 to 0/100). Yield: 1.1 g of intermediate D4 (S-enantiomer).

Description 5

1-(2-Chloro-6-methyl-pyridine-4-carbonyl)-3-(3-methoxy-5-trifluoromethyl-phenyl)-thiourea (D5)

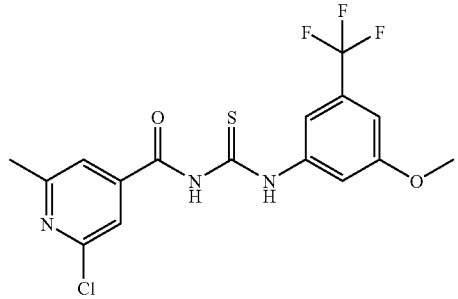

Sodium thiocyanate (6.998 g, 0.08632 mol) was added to a solution of 2-chloro-6-methyl-4-pyridinecarbonyl chloride (14.912 g, 0.078472 mol) in acetone (2 l). The resulting mixture was stirred for 1 hour at room temperature (formation of a brown precipitate). Subsequently, 3-methoxy-5-trifluoromethyl benzenamine (15 g, 0.078472 mol) was added dropwise and the reaction mixture was stirred for 2 hours at room temperature (brown precipitate). The mixture was dissolved in $CH_2Cl_2$ (1.5 l) and was then washed with 2×250 ml water and brine. The separated organic layer was evaporated and the residue was triturated overnight with DIPE/heptane. The product was filtered off and dried in vacuo. Yield: 21.32 g of intermediate D5 (67%).

Description 6

1-(2-Chloro-6-methyl-pyridine-4-carbonyl)-3-(3-methoxy-5-trifluoromethyl-phenyl)-2-methyl-isothiourea (D6)

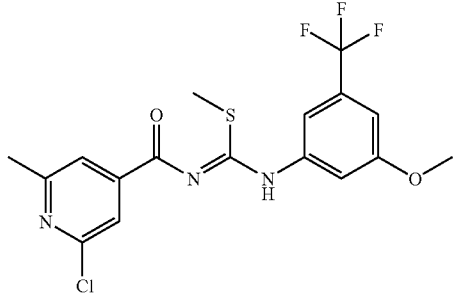

(Reaction performed under $N_2$ atmosphere) NaH (1.267 g, 0.05279 mol) was added portionwise to an ice-cooled solution of intermediate D5 (21.32 g, 0.05279 mol) in THF (480 ml) and the resulting mixture was stirred for 15 minutes at 0° C. Subsequently, a solution of $CH_3I$ (7.493 g, 0.05279 mol) in THF (40 ml) was added dropwise and the mixture was stirred for 2 hours at room temperature. Then the reaction mixture was quenched with $H_2O$ and extracted with $CH_2Cl_2$ (3×500 ml). The organic layers were separated, combined, washed with brine, dried ($MgSO_4$), filtered and the solvent was evaporated in vacuo. The crude product was triturated with DIPE/heptane. The off-white solid was filtered off and dried to yield 16.203 g of intermediate D6 (73.5%). Heptane and $H_2O$ were added to the filtrate and this mixture was stirred overnight at room temperature. The off-white precipitate was filtered off and dried to yield more (1.957 g) of intermediate D6 (9%).

Description 7

(S)-1-[5-(2-Chloro-6-methyl-pyridin-4-yl)-3-(3-methoxy-5-trifluoromethyl-phenylamino)-[1,2,4]triazol-1-yl]butan-2-ol (D7)

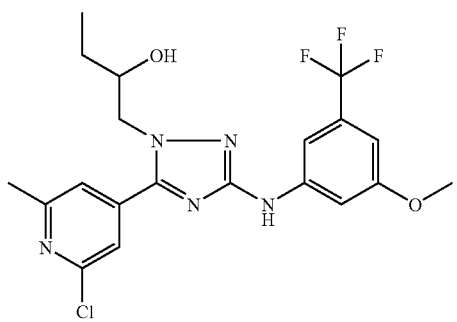

A mixture of intermediate D6 (8.356 g, 0.020 mol) and intermediate D3 (2.083 g, 0.020 mol) in ethanol (200 ml) was stirred overnight at reflux. Subsequently, the solvent was evaporated to yield intermediate D7 (S-enantiomer) as a yellow oil that was used as such in the next reaction step.

Description 8

Acetic acid (S)-1-[5-(2-chloro-6-methyl-pyridin-4-yl)-3-(3-methoxy-5-trifluoromethyl-phenylamino)-[1,2,4]triazol-1-ylmethyl]-propyl ester (D8)

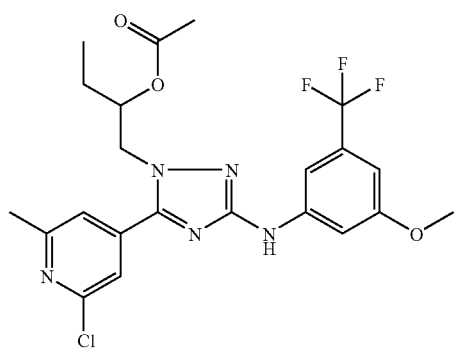

N,N-Dimethyl-4-pyridinamine (0.1222 g, 0.001 mol) was added to a solution of intermediate D7 (9.117 g, 0.020 mol) in acetyl acetate (378 ml). The reaction mixture was stirred at reflux for 30 minutes. Subsequently, the mixture was cooled to room temperature and the solvent was evaporated in vacuo. The residue was redissolved in $CH_2Cl_2$. This organic solution was washed with a saturated sodium bicarbonate solution, washed with brine, and was subsequently dried ($MgSO_4$), filtered and the solvent was evaporated in vacuo. The obtained yellow oil was purified by reversed-phase high-performance liquid chromatography (Shandon Hyperprep® C18 BDS (Base Deactivated Silica) 8 μm, 250 g, I.D. 5 cm). A gradient with 3 mobile phases was applied. Phase A: a 0.25% $NH_4HCO_3$ solution in water; phase B: methanol; phase C: $CH_3CN$). The desired fractions were collected. The solvent was evaporated and co-evaporated with methanol. The product was crystallized from DIPE/heptane. The white crystals were filtered off and dried in vacuo. Yield: 3.677 g of intermediate D8 (37%; 5-enantiomer).

Description 9

1-(2,6-Dichloro-pyridine-4-carbonyl)-3-(2,3,4-trifluoro-phenyl)-thiourea (D9)

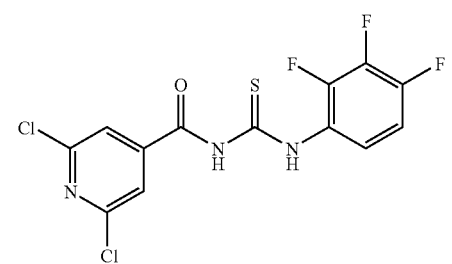 [SMILES: O=C(NC(=S)Nc1ccc(F)c(F)c1F)c1cc(Cl)nc(Cl)c1]

Ammonium isothiocyanate (7.726 g, 0.1015 mol) was added to a solution of 2,6-dichloro-4-pyridinecarbonyl chloride (17.8 g, 0.0846 mol) in acetone (300 ml). The mixture was stirred for 30 minutes and subsequently 2,3,4-trifluorobenzenamine hydrochloric acid (.HCl) was added slowly. The reaction mixture was stirred at room temperature for 2 hours and was then quenched with H$_2$O (100 ml). The mixture was extracted with CH$_2$Cl$_2$ (3×80 ml) and the combined organic layers were dried (MgSO$_4$), filtered and the solvent was evaporated in vacuo. The residue was purified by flash chromatography (eluent: heptane/EtOAc from 80/20 to 50/50). The desired fractions were collected and the solvent was evaporated in vacuo. Yield: 22.2 g of intermediate D9 (69%).

Description 10

1-(2,6-Dichloro-pyridine-4-carbonyl)-2-methyl-3-(2,3,4-trifluoro-phenyl)isothiourea (D10)

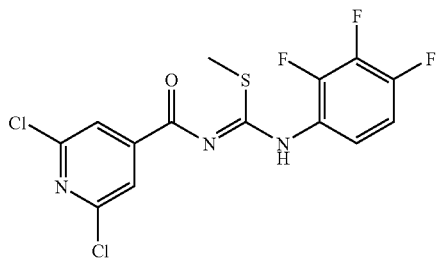 [SMILES: CS/C(=N\C(=O)c1cc(Cl)nc(Cl)c1)Nc1ccc(F)c(F)c1F]

NaH (2.70 g, 0.06747 mol) was added carefully to a cooled solution (0° C.) of intermediate D9 (28.5 g, 0.04498 mol) in THF (200 ml). The mixture was stirred for 15 minutes and then CH$_3$I (6.38 g, 0.04498 mol) was added. The ice-bath was removed and the reaction mixture was stirred for 2 hours at room temperature. Subsequently, the mixture was quenched with H$_2$O and extracted with CH$_2$Cl$_2$ (3×100 ml). The combined organic layers were washed (brine), dried (MgSO$_4$), filtered and the solvent was evaporated in vacuo. The residue was purified by flash chromatography (eluent: heptane/EtOAc gradiënt from 80/20 to 50/50). The desired fractions were collected and the solvent was evaporated. Yield: 5.7 g of intermediate D10 (32%).

Description 11

(S)-1-[5-(2,6-Dichloro-pyridin-4-yl)-3-(2,3,4-trifluoro-phenylamino)-[1,2,4]triazol-1-yl]-butan-2-ol (D11)

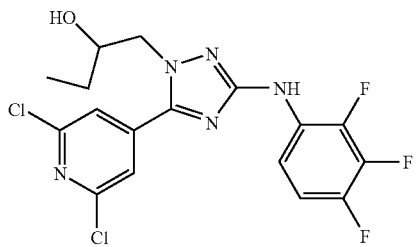 [SMILES: CCC(O)Cn1nc(Nc2ccc(F)c(F)c2F)nc1-c1cc(Cl)nc(Cl)c1]

Intermediate D3 (0.143 g, 0.00137 mol) was added to a solution of intermediate D10 (0.3 g, 0.000457 mol) in t-BuOH (40 ml). The reaction mixture was stirred overnight at reflux. The solvent was evaporated in vacuo and the residue was purified by flash column chromatography over silica gel (eluent: EtOAc/heptane gradient from 20/80 to 50/50). The desired fractions were collected and the solvent was evaporated. Yield: 0.160 g of intermediate D11 (81%; S-enantiomer).

Description 12

(S)-1-[3-(3-Chloro-2-fluoro-phenylamino)-5-(2,6-dichloro-pyridin-4-yl)-[1,2,4]triazol-1-yl]butan-2-ol (D12)

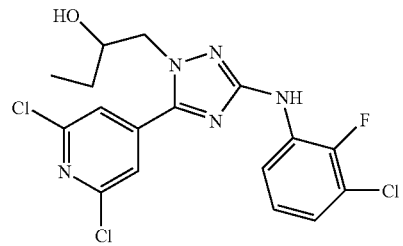 [SMILES: CCC(O)Cn1nc(Nc2cccc(Cl)c2F)nc1-c1cc(Cl)nc(Cl)c1]

Intermediate D12 was prepared according to a procedure analogous to the procedure used for the synthesis of D11. Yield: Intermediate D12 (79%; S-enantiomer).

Description 13

1-(2-Chloro-6-methyl-pyridine-4-carbonyl)-3-(3-fluoro-5-methoxy-phenyl)thiourea (D13)

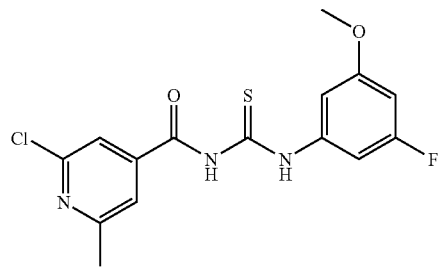 [SMILES: COc1cc(F)cc(NC(=S)NC(=O)c2cc(C)nc(Cl)c2)c1]

2-Chloro-6-methyl-4-pyridinecarbonyl chloride (44.087 g, 0.232 mol) in acetone (1 l) was treated with ammonium isothiocyanate (21.192 g, 0.278 mol) and the mixture was stirred for 1 hour at room temperature. Subsequently, a solution of 3-fluoro-5-methoxybenzenamine (36.02 g, 0.255 mol) in acetone (200 ml) was added dropwise and the reaction mixture was stirred for 4 hours at room temperature. The solvent was evaporated in vacuo and the residue was dissolved in CH$_2$Cl$_2$ (1 l). This organic solution was washed (H$_2$O), dried (MgSO$_4$), filtered and the solvent was evaporated in vacuo to yield a brown solid. The brown solid was triturated in acetonitrile (0.8 l), stirred overnight and the solid was filtered off and dried (vacuum oven, 4 hours at 65° C.). Yield: 59.69 g of intermediate D13 (73%).

Description 14

1-(2-Chloro-6-methyl-pyridine-4-carbonyl)-3-(3-fluoro-5-methoxy-phenyl)-2-methyl-isothiourea (D14)

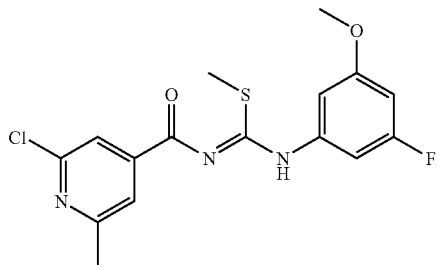 [SMILES: COc1cc(F)cc(N/C(=N/C(=O)c2cc(C)nc(Cl)c2)SC)c1]

NaH 60% in parafine (10.123 g, 0.253 mol) was added portionwise to an ice-cooled solution of intermediate D13 (59.69 g, 0.169 mol) in THF (1000 ml). After 15 minutes, CH$_3$I (15.651 ml) dissolved in THF (200 ml) was added dropwise. The reaction mixture was stirred overnight at room temperature and was then quenched with H$_2$O (25 ml). After work up and evaporation of the solvent, the solid was triturated with DIPE (0.5 l) and CH$_3$CN (50 ml). The mixture was stirred for 3 hours and then the product was filtered off and dissolved in CH$_2$Cl$_2$ (1.5 l). The organic solution was washed with H$_2$O (0.8 l), dried (MgSO$_4$), filtered and the solvent was evaporated in vacuo. Yield: 52.3 g of intermediate D14 (84.3%).

Description 15

(S)-1-[5-(2-Chloro-6-methyl-pyridin-4-yl)-3-(3-fluoro-5-methoxy-phenylamino)-[1,2,4]triazol-1-yl]butan-2-ol (D15)

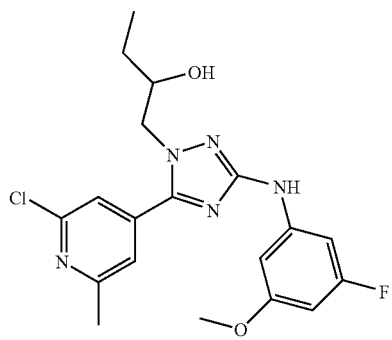 [SMILES: CCC(O)Cn1nc(Nc2cc(F)cc(OC)c2)nc1-c1cc(C)nc(Cl)c1]

A mixture of intermediate D3 (22.213 g, 0.213 mol), intermediate D14 (52.3 g, 0.142 mol) and ethanol (500 ml) was refluxed for 16 hours while the mixture was purged with N$_2$. The mixture was quenched with a NaOCl solution. Subsequently, the solvent was evaporated in vacuo and the residue was crystallized from DIPE (400 ml). A light yellow solid was filtered off and was used as such in the next reaction step. Yield: 33.124 g of intermediate D15 (57.4%; S-enantiomer).

B. Preparation of the Compounds

Example B1

(S)-1-[3-(3,4-Difluoro-phenylamino)-5-(2,6-dimethyl-pyridin-4-yl)-[1,2,4]triazol-1-yl]-butan-2-ol (E1)

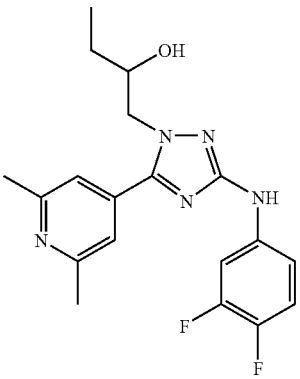 [SMILES: CCC(O)Cn1nc(Nc2ccc(F)c(F)c2)nc1-c1cc(C)nc(C)c1]

Intermediate D4 (1.1 g, 2.80 mmol) was dissolved in THF (15 ml) and iron(III) acetylacetonate (0.099 g, 0.28 mmol) and NMP (1 ml) were added. The reaction mixture was then cooled to 0° C. Under N$_2$ (gas) protection, CH$_3$MgBr 3M in Et$_2$O (4 ml, 12 mmol) was added slowly. The reaction mixture was warmed to room temperature and stirred for one hour until the reaction was finished. The reaction mixture was then quenched with saturated NH$_4$Cl solution and then extracted by CH$_2$Cl$_2$ (3×30 ml). The combined organic phase was washed by brine, dried over MgSO$_4$, filtered and the solvent was evaporated in vacuo. The residue was purified by reversed-phase high-performance liquid chromatography (Shandon Hyperprep® C18 BDS (Base Deactivated Silica) 8 µm, 250 g, I.D. 5 cm). A gradient with 2 or 3 mobile phases was applied (phase A: a 0.25% NH$_4$HCO$_3$ solution in water; phase B: CH$_3$OH (optional); phase C: CH$_3$CN).
Yield: 0.152 g of compound E1 (S-enantiomer).

Example B2

(S)-1-[3-(3-Chloro-phenylamino)-5-(2-ethylamino-pyridin-4-yl)-[1,2,4]triazol-1-yl]-butan-2-ol (E2)

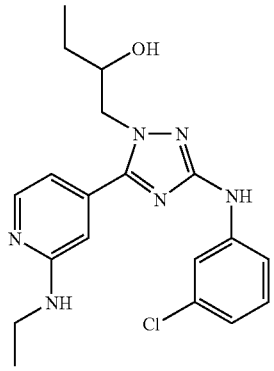 [SMILES: CCNc1cc(-c2nc(Nc3cccc(Cl)c3)nn2CC(O)CC)ccn1]

Intermediate 1-[3-(3-chloro-phenylamino)-5-(2-chloro-pyridin-4-yl)-[1,2,4]triazol-1-yl]-butan-2-ol (prepared according to description 4) (1.15 g; 3.04 mmol) was dissolved in CH$_3$OH (20 ml) and then ethylamine (3 g) was added. The reaction mixture was stirred for 16 hours at 160° C. under pressure (until the reaction had proceeded to completion).

The solvent was then evaporated in vacuo. The residue was purified by reversed-phase high-performance liquid chromatography (Shandon Hyperprep® C18 BDS (Base Deactivated Silica) 8 μm, 250 g, I.D. 5 cm). A gradient with 2 mobile phases was applied (phase A: a 0.25% NH$_4$HCO$_3$ solution in water; phase B: CH$_3$CN). The desired fractions were collected, worked-up and finally the residue was crystallized from diisopropyl ether. Yield: 0.1595 g of compound E2 (S-enantiomer).

Example B3

1-[3-(3,4-Difluoro-phenylamino)-5-(2-methyl-pyridin-4-yl)-[1,2,4]triazol-1-yl]-hexan-2-ol (E3)

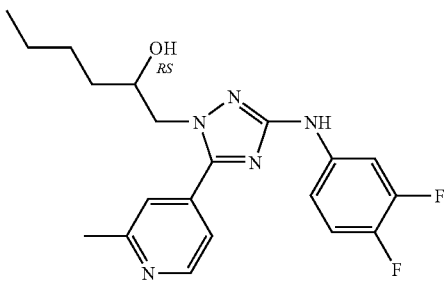 [SMILES: CCCCC(O)Cn1nc(Nc2ccc(F)c(F)c2)nc1-c1ccnc(C)c1]

A mixture of intermediate, 1-[5-(2-chloro-6-methyl-pyridin-4-yl)-3-(3,4-difluoro-phenylamino)-[1,2,4]triazol-1-yl]-hexan-2-ol (prepared according to D4) (1.5 g; 3.5 mmol) and Et$_3$N (2 ml) in THF (40 ml) was hydrogenated with Pd/C 10% (0.020 g) as a catalyst in the presence of thiophene solution (0.1 ml; 4% in DIPE). After uptake of H$_2$ (1 equiv) had ceased, the catalyst was filtered off and the filtrate was evaporated in vacuo. The residue was suspended in DIPE and filtrated. The crystals were dried in a vacuum oven at 70° C. overnight.

Yield: 876 mg of compound E3 (65%).

Example B4

(−)-1-[3-(3,4-Difluoro-phenylamino)-5-(2,6-dimethyl-pyridin-4-yl)-[1,2,4]triazol-1-yl]-hexan-2-ol (E4) and (+)-1-[3-(3,4-Difluoro-phenylamino)-5-(2,6-dimethyl-pyridin-4-yl)-[1,2,4]triazol-1-yl]-hexan-2-ol (E5)

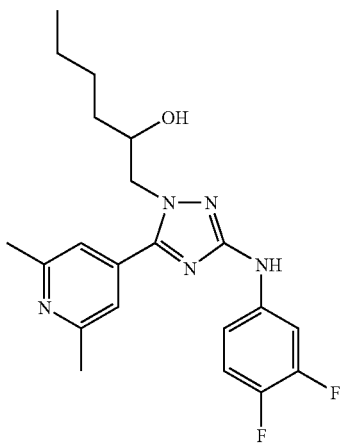

(-)-E4

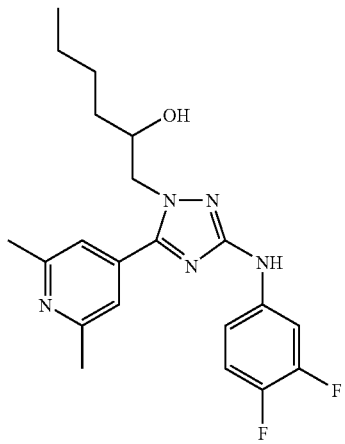

(+)-E5

Compound E7 (564 mg; 1.4 mmol) was separated into enantiomers by Supercritical Fluid Chromatography (SFC) on a Chiralpak AD-H column (30×250 mm) with a flow rate of 50 ml/min. A mixture of 30% CH$_3$OH (+0.2% 2-propylamine)/70% CO$_2$ was used as the eluent. The column heater was set at 40° C. and the nozzle pressure was set at 100 bar.

The first eluting isomer, peak "A", was collected and concentrated, the oily residue was triturated from a mixture of DIPE and heptane. A white solid was collected by filtration, washed with heptane and dried in a vacuum oven. Yield: 200 mg of compound E4 as a white powder (crystalline).

The second eluting isomer, peak "B", was collected and concentrated, the oily residue was triturated from a mixture of DIPE and heptane. A white solid was collected by filtration, washed with heptane and dried in vacuum oven. Yield: 212 mg of compound E5 as a white powder (crystalline).

Example B5

(S)-1-[5-(2,6-Dimethyl-pyridin-4-yl)-3-(3-methoxy-5-trifluoromethyl-phenylamino)-[1,2,4]triazol-1-yl]-butan-2-ol (E30)

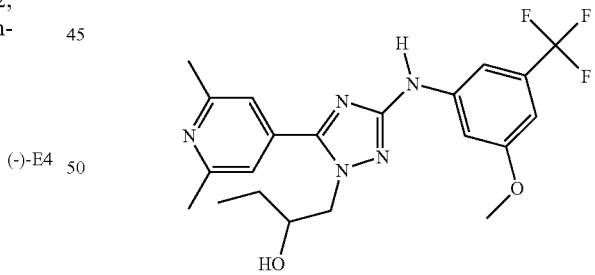

NMP (1 ml; extra dry) and iron(III) acetylacetonate (35.33 g, 0.0001 mol) were added to a solution of intermediate D8 (498.08 g, 0.001 mol) in THF (10 ml; extra dry) and the mixture was cooled to 0° C. Methylmagnesium bromide (1.67 ml, 0.005 mol) was added slowly and the reaction mixture was stirred for 5 minutes at 0° C. Subsequently, the mixture was quenched with a saturated NH$_4$Cl solution and extracted with CH$_2$Cl$_2$ (3×50 ml). The combined organic layers were washed with brine, dried (MgSO$_4$), filtered and the solvent was evaporated. The residue was redissolved in methanol and NaOH (800 mg, 0.020 mol) was added. The resulting mixture was stirred for 1 hour at room temperature.

A saturated NH$_4$Cl solution was added and the mixture was extracted with CH$_2$Cl$_2$ (3×50 ml). The combined organic layers were washed (brine), dried (MgSO$_4$), filtered and the solvent was evaporated in vacuo. The residue was purified by flash column chromatography over silica gel (eluent: (7 N NH$_3$/MeOH)/CH$_2$Cl$_2$ gradiënt from 0/100 to 10/90. The product fractions were collected and the solvent was evaporated in vacuo. The residue was treated with heptane, yielding white crystals. These white crystals were filtered off and dried in vacuo. Yield: 0.632 g of compound E30 (83%; S-enantiomer).

Example B6

(S)-1-[5-(2,6-Dimethyl-pyridin-4-yl)-3-(2,3,4-trifluoro-phenylamino)-[1,2,4]triazol-1-yl]-butan-2-ol (E32) and (S)-1-[5-(2-Chloro-6-methyl-pyridin-4-yl)-3-(2,3,4-trifluoro-phenylamino)-[1,2,4]triazol-1-yl]butan-2-ol (D16)

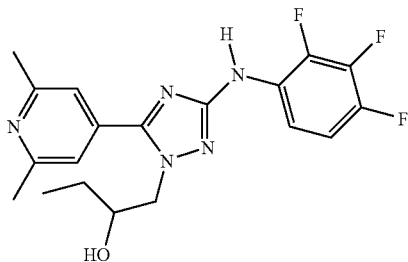

E32 (S-enantiomer)

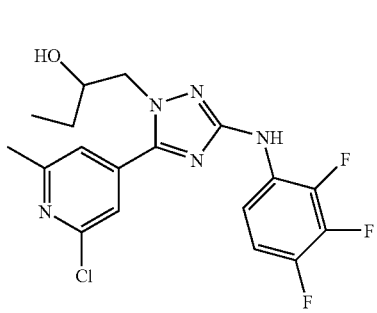

D16 (S-enantiomer)

A mixture of intermediate D11 (0.47 g, 0.0011 mol), iron (III) acetylacetonate (0.0383 g, 0.00011 mol), NMP (1 ml) and THF (25 ml) was stirred at 0° C. CH$_3$MgBr 3 M in Et$_2$O (2.9 ml, 0.0087 mol) was added. The reaction mixture was stirred for 2 hours at room temperature. The mixture was quenched with a saturated NH$_4$Cl solution and extracted with CH$_2$Cl$_2$ (3×30 ml). The organic layer was washed (brine), dried (MgSO$_4$), filtered and the solvent was evaporated in vacuo. The residue was purified by reversed-phase high-performance liquid chromatography (Shandon Hyperprep® C18 BDS (Base Deactivated Silica) 8 μm, 250 g, I.D. 5 cm). A gradient with 3 mobile phases was applied. Phase A: a 0.25% NH$_4$HCO$_3$ solution in water; phase B: methanol; phase C: CH$_3$CN). Two different product fractions were collected and worked-up. Yield: 0.077 g of intermediate D16 (17%). Yield: 0.183 g of compound E32 (43%; S-enantiomer).

A part of compound E32 was converted into the HCl salt by standard methods obvious to those skilled in the art to yield compound E33 (HCl salt; S-enantiomer).

Example B7

(S)-1-[5-(2-Methyl-pyridin-4-yl)-3-(2,3,4-trifluoro-phenylamino)-[1,2,4]-triazol-1-yl]-butan-2-ol (E31)

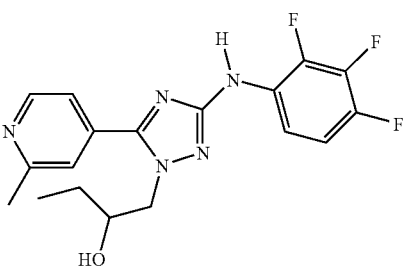 [SMILES: CCC(O)Cn1nc(Nc2ccc(F)c(F)c2F)nc1-c1ccnc(C)c1]

A mixture of intermediate D16 (0.13 g, 0.000316 mol), [1,3-bis[2,6-bis(1-methylethyl)phenyl]-2-imidazolidinylidene]chloro(η3-2-propenyl)palladium (CAS [478980-01-7]; catalyst) (0.01814 g, 0.0000316 mol) and NaOCH$_3$ (0.5 M in methanol) (1 ml) in 2-propanol (4 ml) was stirred under microwave irradiation for 10 minutes at 120° C. The solvent was evaporated and the concentrate was washed with H$_2$O and extracted with CH$_2$Cl$_2$. The organic layer was dried (MgSO$_4$), filtered and the solvent was evaporated in vacuo.

The residue was purified by reversed-phase high-performance liquid chromatography (Shandon Hyperprep® C18 BDS (Base Deactivated Silica) 8 µm, 250 g, I.D. 5 cm). A gradient with 3 mobile phases was applied. Phase A: a 0.25% $NH_4HCO_3$ solution in water; phase B: methanol; phase C: $CH_3CN$). The desired fractions were collected and worked-up. Yield: 0.0519 g of compound E31 (43.5%; S-enantiomer).

Example B8

(S)-1-[3-(3-Chloro-2-fluoro-phenylamino)-5-(2,6-dimethyl-pyridin-4-yl)-[1,2,4]-triazol-1-yl]-butan-2-ol HCl salt (E35)

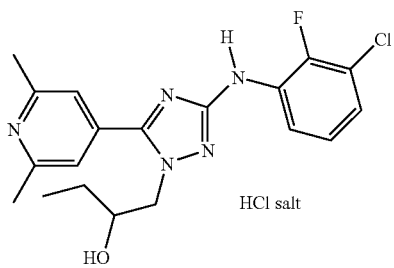 [SMILES: CCC(O)Cn1nc(Nc2cccc(Cl)c2F)nc1-c1cc(C)nc(C)c1]

HCl salt

A mixture of intermediate D12 (2.6 g, 0.00604 mol), iron (III) acetylacetonate (0.427 g, 0.00121 mol), THF (150 ml) and NMP (35 ml) was stirred at 0° C. $CH_3MgBr$ 3 M in $Et_2O$ (10 ml) was added and the mixture was stirred for 1 hour at room temperature. More $CH_3MgBr$ 3 M in $Et_2O$ (10 ml) and methanol were added. The solvent was evaporated and $CH_2Cl_2$ and $H_2O$ (few ml) were added to the residue. The mixture was filtered over diatomaceous earth. The filtrate was evaporated and the residue was dissolved in DIPE. This solution was washed ($H_2O$) and the organic layer was dried ($MgSO_4$), filtered and the solvent was evaporated in vacuo. The residue was dissolved in 2-propanol and HCl/2-propanol was added to the solution while cooling on an ice-bath. Subsequently, the solvent was evaporated and the residue was stirred in acetone. The crystals were filtered off and dried. Yield: 0.96 g of compound E35 (37%; S-enantiomer; HCl-salt). An extra amount of compound E35 could be obtained from the filtrate, to result in a total yield of 63%.

Example B9

(S)-1-[3-(3-Fluoro-5-methoxy-phenylamino)-5-(2-methyl-pyridin-4-yl)-[1,2,4]triazol-1-yl]butan-2-ol HCl salt (E36) and (E38) (free base of E36)

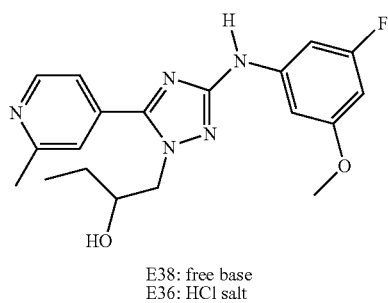 [SMILES: CCC(O)Cn1nc(Nc2cc(F)cc(OC)c2)nc1-c1ccnc(C)c1]

E38: free base
E36: HCl salt

A mixture of intermediate D15 (0.406 g, 0.001 mol), [1,3-bis[2,6-bis(1-methylethyl)phenyl]-2-imidazolidinylidene]chloro(η3-2-propenyl)palladium (CAS [478980-01-7]; catalyst) (0.055 g, 0.0000957 mol) and NaOMe (0.2 ml of a 5.33 M solution in MeOH, 0.001066 mol) in 2-propanol (10 ml) was heated in a microwave for 10 minutes at 120° C. Subsequently the reaction mixture was concentrated in vacuo, diluted with $CH_2Cl_2$ and washed with $H_2O$. The organic layer was dried ($MgSO_4$), filtered and the solvent was evaporated in vacuo. The residue was purified by column chromatography (eluent: $CH_2Cl_2$/MeOH 100/0-95/5). The desired fractions were collected and the solvent was evaporated to yield 0.300 g of a colorless oil (compound E38, which is the free base of compound E36). Compound E38 (S-enantiomer) was converted into its HCl salt: The oil was dissolved in DIPE and treated with 6 N HCl in 2-propanol and this mixture was stirred for 5 hours. A yellow precipitate was filtered off and dried (vacuum oven, 65° C., 3 days). Yield: 0.237 g of compound E36 (58%; S-enantiomer; HCl-salt).

Table 1 and 2 lists compounds of Formula (I) that were prepared in analogy to one of the above Examples (Ex. no.).

TABLE 1

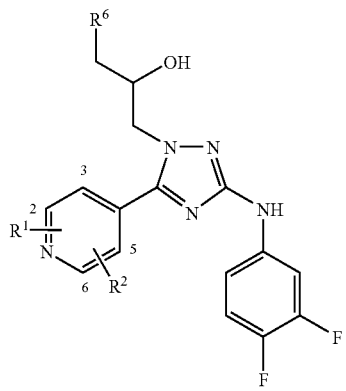

| Comp. No. | Ex. No. | R¹ | R² | R⁶ | Stereochemical information |
|---|---|---|---|---|---|
| E6 | B1 | 2-CH$_3$ | H | —CH$_3$ | (+)-S-enantiomer |
| E26 | B1 | 2-CH$_3$ | H | —CH$_3$ | (−)-R-enantiomer |
| E10 | B3 | 2-CH$_3$ | H | —CH$_2$CH$_3$ | racemic mixture |
| E15 | B4 | 2-CH$_3$ | H | —CH$_2$CH$_3$ | (−)-enantiomer |
| E16 | B4 | 2-CH$_3$ | H | —CH$_2$CH$_3$ | (+)-enantiomer |
| E3 | B3 | 2-CH$_3$ | H | —CH$_2$CH$_2$CH$_3$ | racemic mixture |
| E11 | B4 | 2-CH$_3$ | H | —CH$_2$CH$_2$CH$_3$ | (−)-enantiomer |
| E12 | B4 | 2-CH$_3$ | H | —CH$_2$CH$_2$CH$_3$ | (+)-enantiomer |
| E1 | B1 | 2-CH$_3$ | 6-CH$_3$ | —CH$_3$ | (+)-S-enantiomer |
| E27 | B1 | 2-CH$_3$ | 6-CH$_3$ | —CH$_3$ | (−)-R-enantiomer |
| E8 | B1 | 2-CH$_3$ | 6-CH$_3$ | —CH$_2$CH$_3$ | racemic mixture |
| E13 | B4 | 2-CH$_3$ | 6-CH$_3$ | —CH$_2$CH$_3$ | (−)-enantiomer |
| E14 | B4 | 2-CH$_3$ | 6-CH$_3$ | —CH$_2$CH$_3$ | (+)-enantiomer |
| E7 | B1 | 2-CH$_3$ | 6-CH$_3$ | —CH$_2$CH$_2$CH$_3$ | racemic mixture |
| E4 | B4 | 2-CH$_3$ | 6-CH$_3$ | —CH$_2$CH$_2$CH$_3$ | (−)-enantiomer |
| E5 | B4 | 2-CH$_3$ | 6-CH$_3$ | —CH$_2$CH$_2$CH$_3$ | (+)-enantiomer |
| E9 | B2 | 2-NHCH$_2$CH$_2$OCH$_3$ | H | —CH$_3$ | (+)-S-enantiomer |
| E25 | B2 | 2-NHCH$_2$CH$_3$ | H | —CH$_3$ | (−)-R-enantiomer |

TABLE 2

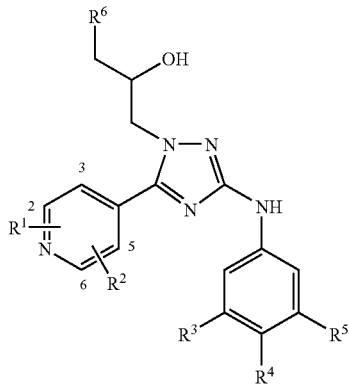

| Comp. No. | Ex. No. | R¹ | R² | R³ | R⁴ | R⁵ | R⁶ | stereochemical information and salt form |
|---|---|---|---|---|---|---|---|---|
| E17 | B1 | 2-CH$_3$ | H | Cl | H | H | —CH$_3$ | (+)-S-enantiomer |
| E19 | B1 | 2-CH$_3$ | H | —CH$_3$ | F | H | —CH$_3$ | (+)-S-enantiomer |
| E38 | B9 | 2-CH$_3$ | H | F | H | —OCH$_3$ | —CH$_3$ | S-enantiomer |
| E36 | B9 | 2-CH$_3$ | H | F | H | —OCH$_3$ | —CH$_3$ | S-enantiomer HCl salt |
| E20 | B1 | 2-CH$_3$ | H | —CF$_3$ | H | —OCH$_3$ | —CH$_3$ | (+)-S-enantiomer |
| E28 | B1 | 2-CH$_3$ | H | —CF$_3$ | H | —OCH$_3$ | —CH$_3$ | (−)-R-enantiomer |
| E18 | B1 | 2-CH$_3$ | 6-CH$_3$ | Cl | H | H | —CH$_3$ | (−)-R-enantiomer |
| E21 | B1 | 2-CH$_3$ | 6-CH$_3$ | Cl | H | H | —CH$_3$ | (+)-S-enantiomer |
| E22 | B3 | 2-CH$_3$ | 6-CH$_3$ | Cl | H | H | —CH$_2$CH$_3$ | racemic mixture |
| E23 | B4 | 2-CH$_3$ | 6-CH$_3$ | Cl | H | H | —CH$_2$CH$_3$ | (−)-enantiomer |

TABLE 2-continued

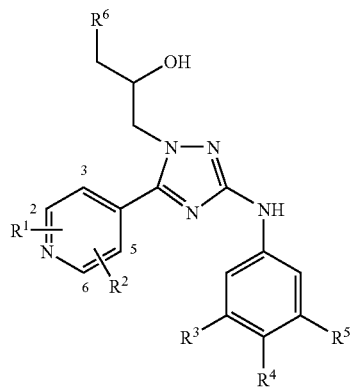

| Comp. No. | Ex. No. | $R^1$ | $R^2$ | $R^3$ | $R^4$ | $R^5$ | $R^6$ | stereochemical information and salt form |
|---|---|---|---|---|---|---|---|---|
| E24 | B4 | 2-$CH_3$ | 6-$CH_3$ | Cl | H | H | —$CH_2CH_3$ | (+)-enantiomer |
| E39 | B5 | 2-$CH_3$ | 6-$CH_3$ | F | H | —$OCH_3$ | —$CH_3$ | (+)-S-enantiomer |
| E37 | B5 | 2-$CH_3$ | 6-$CH_3$ | F | H | —$OCH_3$ | —$CH_3$ | (+)-S-enantiomer HCl salt |
| E30 | B5 | 2-$CH_3$ | 6-$CH_3$ | —$CF_3$ | H | —$OCH_3$ | —$CH_3$ | (+)-S-enantiomer |
| E29 | B2 | 2-$NHCH_2CH_3$ | H | Cl | H | H | —$CH_3$ | (−)-R-enantiomer |
| E2 | B2 | 2-$NHCH_2CH_3$ | H | Cl | H | H | —$CH_3$ | (+)-S-enantiomer |

TABLE 3

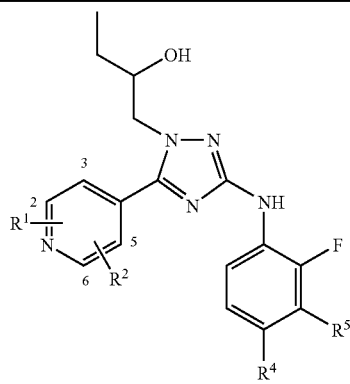

| Comp. No. | Ex. No. | $R^1$ | $R^2$ | $R^4$ | $R^5$ | stereochemical information and salt form |
|---|---|---|---|---|---|---|
| E31 | B7 | 2-$CH_3$ | H | F | F | S-enantiomer |
| E34 | B6 | 2-$CH_3$ | 6-$CH_3$ | H | Cl | S-enantiomer |
| E35 | B8 | 2-$CH_3$ | 6-$CH_3$ | H | Cl | S-enantiomer HCl Salt |
| E32 | B6 | 2-$CH_3$ | 6-$CH_3$ | F | F | S-enantiomer |
| E33 | B6 | 2-$CH_3$ | 6-$CH_3$ | F | F | S-enantiomer HCl Salt |

C. Analytical Part

LCMS
General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS—Procedure 1

In addition to general procedure A: Reversed phase HPLC was carried out on an Xterra MS C18 column (3.5 μm, 4.6× 100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Procedure 2

In addition to general procedure A: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Procedure 3

In addition to general procedure A: Reversed phase HPLC was carried out on an Atlantis C18 column (3.5 μm, 4.6×100 mm) (3.5 μm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 μl was used. Cone voltage was 10 V for positive ionization mode and 20 V for negative ionization mode.

LCMS—Procedure 4 (Only Used for Intermediates: D1, D2 and D4)

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 μl was used. Cone voltage was 10 V for positive ionization mode and 20 V for negative ionization mode.

LCMS—Procedure 5

In addition to general procedure A: Column heater was set at 45° C. Reversed phase HPLC was carried out on an Atlantis C18 column (3.5 μm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 9 minutes and hold these conditions for 3 minutes. An injection volume of 10 μl was used. Cone voltage was 10 V for positive ionization mode and 20 V for negative ionization mode.

LCMS—Procedure 6

In addition to general procedure B: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Melting Points

For a number of compounds, melting points (m.p.) were determined with a DSC823e (Mettler-Toledo). Melting points were measured with a temperature gradient of 30° C./minute. Maximum temperature was 400° C.

Values are obtained with experimental uncertainties that are commonly associated with this analytical method.

TABLE 4

Analytical data - Retention time ($R_t$ in minutes), [M − H]⁻ peak and LCMS procedure.

| Co. Nr. | $R_t$ | [M − H]⁻ | LCMS Procedure |
|---|---|---|---|
| D1 | 1.07 | 340 | 4 |
| D4 | 0.97 | 392 | 4 |

When a compound is a mixture of isomers which gave different peaks in the LCMS method, only the retention time of the main component is given in the LCMS table.

TABLE 5

Analytical data - Retention time ($R_t$ in minutes), [M + H]⁺ peak, LCMS procedure and melting points (m.p. is defined as melting point).

| Co. Nr. | $R_t$ | [M + H]⁺ | LCMS Procedure | m.p. (° C.) |
|---|---|---|---|---|
| D2 | 1.04 | 356 | 4 | n.d. |
| E6 | 5.33 | 360 | 1 | 142.72 |
| E1 | 5.51 | 374 | 1 | 166.04 |
| E9 | 5.40 | 419 | 1 | 137.06 |
| E15 | 5.64 | 374 | 1 | 133.10 |
| E16 | 5.65 | 374 | 1 | 134.82 |
| E5 | 7.66 | 402 | 3 | 135.00 |
| E4 | 7.68 | 402 | 3 | 134.60 |
| E12 | 8.04 | 388 | 3 | 120.50 |
| E11 | 8.03 | 388 | 3 | 121.64 |
| E2 | 5.67 | 387 | 1 | 161.99 |
| E17 | 5.45 | 358 | 1 | 144.31 |
| E13 | 5.80 | 388 | 1 | 141.14 |
| E14 | 5.81 | 388 | 1 | 139.48 |
| E18 | 7.26 | 372 | 3 | inconclusive |
| E19 | 5.36 | 356 | 1 | 133.85 |
| E20 | 5.76 | 422 | 1 | 120.54 |
| E21 | 7.27 | 372 | 3 | inconclusive |
| E3 | 5.95 | 388 | 1 | 137.96 |
| E22 | 6.01 | 386 | 1 | n.d. |
| E23 | 5.69 | 386 | 2 | 127.44 |
| E24 | 5.70 | 386 | 2 | inconclusive |
| E7 | 6.09 | 402 | 1 | 158.22 |
| E8 | 5.80 | 388 | 1 | 152.48 |
| E10 | 5.64 | 374 | 1 | 161.40 |
| E26 | 5.34 | 360 | 1 | 145.29 |
| E25 | 5.51 | 389 | 1 | 156.18 |
| E27 | 5.47 | 374 | 1 | inconclusive |
| E28 | 8.29 | 422 | 5 | 117.16 |
| E29 | 6.83 | 387 | 5 | 158.66 |
| E30 | 5.96 | 436 | 1 | 166.05 |
| E31 | 5.46 | 378 | 1 | inconclusive |
| E32 | 5.37 | 392 | 2 | inconclusive |
| E33 | 5.38 | 392 | 2 | 237.44 |
| E34 | 5.56 | 390 | 2 | inconclusive |
| E35 | 6.03 | 390 | 1 | inconclusive |
| E36 | 1.20 | 372 | 6 | inconclusive |
| E37 | 6.68 | 386 | 5 | inconclusive |
| E38 | n.d. | n.d. | — | n.d. |
| E39 | n.d. | n.d. | — | n.d. |

When a compound is a mixture of isomers which gave different peaks in the LCMS method, only the retention time of the main component is given in the LCMS table.
n.d.: not determined Optical Rotation:

The optical rotation was measured using a Perkin Elmer 341 polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned.

TABLE 6

Analytical data - Optical Rotation

| Co. No. | $[\alpha]_D^{20}$ | concentration | solvent |
|---|---|---|---|
| E6 | +47.42° | 0.4660 w/v % | MeOH |
| E2 | +51.10° | 0.4286 w/v % | MeOH |
| E1 | +45.63° | 0.4624 w/v % | MeOH |
| E15 | −41.99° | 0.3882 w/v % | MeOH |
| E16 | +41.69° | 0.5494 w/v % | MeOH |
| E17 | +49.47° | 0.2850 w/v % | MeOH |
| E18 | −46.63° | 0.4396 w/v % | MeOH |
| E19 | +44.52° | 0.4358 w/v % | MeOH |
| E5 | +36.74° | 0.3402 w/v % | MeOH |
| E9 | +41.82° | 0.3826 w/v % | MeOH |
| E4 | −36.39° | 0.3188 w/v % | MeOH |
| E12 | +37.42° | 0.3474 w/v % | MeOH |
| E11 | −38.53° | 0.3348 w/v % | MeOH |
| E13 | −40.97° | 0.2880 w/v % | MeOH |
| E26 | −46.37° | 0.3860 w/v % | MeOH |
| E25 | −42.42° | 0.4856 w/v % | MeOH |
| E14 | +38.69° | 0.3076 w/v % | MeOH |
| E20 | +42.58° | 0.4674 w/v % | MeOH |
| E21 | +47.41° | 0.4134 w/v % | MeOH |
| E23 | −44.30° | 0.4740 w/v % | MeOH |
| E24 | +44.62° | 0.4370° w/v % | MeOH |
| E27 | −46.37° | 0.4982° w/v % | MeOH |
| E28 | −42.10° | 0.4822 w/v % | MeOH |
| E29 | −50.75° | 0.3448 w/v % | MeOH |
| E30 | +41.04° | 0.2924 w/v % | MeOH |
| E37 | +24.34° | 0.3944 w/v % | MeOH |

D. Pharmacological Examples

Example D.1

Ca$^{2+}$ Flux Imaging (FDSS)

Materials
a) Assay Buffer
   Hanks buffered saline solution (HBSS, Invitrogen, Belgium), supplemented with 10 mM HEPES (Invitrogen, Belgium), CaCl$_2$ to a final concentration of 5 mM, 0.1% Bovine serum albumin (Sigma-Aldrich NV, Belgium).
b) Calcium-Sensitive Dye—Fluo-4AM
   Fluo-4AM (Molecular Probes, USA) was dissolved in DMSO containing 10% Pluronic acid (Molecular Probes, USA) to give a stock solution which was diluted in assay buffer supplemented with 5 mM probenicid (Sigma, Aldrich NV, Belgium) to give a final concentration of 2 µM.
c) 384-Well Plates
   Black 384 well plate black/clear plates, PDL pre-coated (Corning, Incorporated, USA)
d) Calcium Flux Measurement
   A Functional drug screening system (FDSS, Hamamatsu) was used to measure intracellular free-calcium flux signals.
Method
   Monolayers of hα7-wt nAChR-expressing GH4C1 cells were grown in multi-well plates, in particular black-sided, transparent bottomed 384 well plates coated with poly-D-lysine for 24 hours prior to loading with a fluorescent calcium indicator, in a particular embodiment loading with fluo-4AM for up to 120 minutes.
   PAM activity was detected in real time by applying the compound to be tested to the loaded cells along with a α7 nicotinic receptor agonist during constant monitoring of the cellular calcium mobilization by fluorescence in a FDSS. Compounds giving peak fluorescent responses greater than the response due to agonist alone, were considered to be α7 nAChR PAM's. In a particular embodiment, the α7 nicotinic receptor agonist was choline, a more particular embodiment choline applied at a sub-maximal concentration of 100 µM. In a further setting of the present invention the compounds to be tested were applied prior to the α7 nicotinic receptor agonist, in a particular embodiment up to 10 minutes prior to the agonist.
   A control response to choline was calculated on each plate from the difference in peak in fluorescence in wells receiving either choline or assay buffer alone. Compounds of the present invention were tested at a concentration range from 0.01 µM to 30 µM. Compounds were considered to have an interesting activity when they potentiated the choline signal at least with 200% when tested at a concentration of 30 µM (the efficacy of 100 µM choline was defined as 100% in the absence of a PAM).
   EC$_{50}$ values (potency), maximal effect (% efficacy), and Hill slopes were estimated by fitting the sigmoidal equation to the data using GraphPad Prism (GraphPad Software, Inc., San Diego, Calif.). An EC$_{50}$ (or pEC$_{50}$) was determined as a concentration relating to half the maximal effect, when a clear sigmoidal curve with top plateau was obtained.
   The compounds of the present invention also have a potentiating effect on the response to choline when measured by whole-cell voltage-clamp electrophysiology in GH4C1 cells stably over-expressing the human wild-type α7 receptor, as described hereinafter.

Example D.2

Whole-Cell Voltage-Clamp Recording

Whole-cell voltage-clamp recording from mammalian cells has provided a powerful means of assessing the function of membrane proteins thought to be subunits of ligand-gated ion channels. Activation of such proteins by endogenous or exogenous ligands causes opening of a pore associated with the receptor through which ions flow down their electrochemical gradient. In the case of the hα7-wt nAChR-expressing GH4C1 recombinant cell line the preferential permeability to calcium of this receptor means that calcium flows into the cell upon activation by ACh, choline and other nicotinic ligands giving rise to a calcium current. Since this receptor rapidly desensitizes in the presence of an agonist it is important that an application system is used which is capable of very rapid switching of solutions (<100 ms) to prevent partial or full desensitisation of receptor responses coincident with the time of agonist application. Consequently, a second convenient technique to assess the enhancement of nicotinic efficacy is whole-cell voltage-clamp recording from hα7-wt nAChR-expressing GH4C1 cells coupled with a rapid-application system.
Materials
a) Assay Buffers
   The external recording solution consisted of 152 mM NaCl, 5 mM KCl, 1 mM MgCl$_2$, 1 mM Calcium, 10 mM HEPES; pH 7.3. The internal recording solution consisted of 140 mM CsCl, 10 mM HEPES, 10 mM EGTA, 1 mM MgCl$_2$, pH 7.3.
b) Patch-clamp recording was carried out using a Patch-clamp amplifier (Multiclamp 700A, Axon Instruments, CA, USA). The membrane potential of hα7-wt nAChR-expressing GH4C1 cells was voltage-clamped in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1GΩ and series resistance <15 MΩ with at least 60% series resistance compensation. Membrane potential was clamped at −70 mV.

c) Agonists

ACh, choline, were purchased from Sigma-Aldrich NV, Belgium.

d) Compound Application

A 16-channel Dynflow DF-16 microfluidics system (Cellectricon, Sweden) for rapid switching of solutions (switching resolution time <100 ms) was used to apply control, agonist and PAM compounds to hα7-wt nAChR-expressing GH4C1 cells.

Method hα7-wt nAChR-expressing GH4C1 cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (0.75 μl/min) of external recording solution. PAM activity was detected in real time by pre-applying the compounds to be tested to the loaded cells followed by an α7 nicotinic receptor agonist during constant monitoring of cellular membrane current. Compounds giving current responses greater than the response due to agonist alone, were considered to be α7 nAChR PAM's. In a particular embodiment, the α7 nicotinic receptor agonist was activated by a non-selective nicotinic agonist, in a more particular embodiment the agonist was choline, and an even more particular embodiment choline applied at a sub-maximal concentration of 1 mM. In a further setting of the present invention the compounds to be tested were applied prior to the α7 nicotinic receptor agonist, in a more particular embodiment up to 30 seconds prior to the agonist. A control response was calculated from the area under the curve of the current elicited in each cell to an application of submaximal choline for 250 ms. Area under the curve is the integration of net current over time and is a common representation of the total ion flux through the channel. Increases in agonist efficacy elicited by a positive allosteric modulator were calculated as percent potentiation of "area under curve" (AUC) of the agonist response. Potentiation greater than control AUC caused by the compounds of the invention indicates that they are expected to have useful therapeutic activity.

TABLE 7

Potency (pEC$_{50}$) and % efficacy for a number of compounds.

| Compound No. | pEC50 | % Efficacy | PAM_type |
|---|---|---|---|
| E15 | 6.17 | 1580 | 1 |
| E17 | 5.92 | 4040 | 2 |
| E2 | 6.45 | 1150 | 2 |
| E6 | 6.02 | 2200 | 2 |
| E1 | 6.23 | 1680 | 2 |
| E9 | 6.03 | 1000 | 2 |
| E14 | 6.50 | 1400 | 2 |
| E16 | 6.38 | 4580 | 2 |
| E11 | 6.45 | 1150 | 1 |
| E12 | 6.58 | 2160 | 2 |
| E4 | 6.68 | 1010 | n.d. |

TABLE 7-continued

Potency (pEC$_{50}$) and % efficacy for a number of compounds.

| Compound No. | pEC50 | % Efficacy | PAM_type |
|---|---|---|---|
| E5 | 6.69 | 1920 | 2 |
| E13 | 6.61 | 490 | 1 |
| E18 | 5.89 | 1260 | 1 |
| E19 | 5.71 | 2460 | 2 |
| E20 | 6.67 | 4660 | 4 |
| E21 | 6.08 | 3500 | 2 |
| E25 | 6.16 | 1390 | 1 |
| E26 | 6.11 | 580 | 1 |
| E23 | 6.05 | 1640 | 1 |
| E24 | 6.07 | 4570 | 2 |
| E27 | 6.00 | 1270 | 2 |
| E28 | 5.75 | 5210 | 2 |
| E29 | 5.99 | 2010 | 1 |
| E30 | 6.70 | 3940 | 2 |
| E31 | 6.26 | 3050 | 2 |
| E32 | 6.29 | 2600 | 2 |
| E33 | 6.36 | 1560 | n.d. |
| E34 | 6.50 | 2520 | 2 |
| E35 | 6.33 | 1900 | 2 |
| E36 | 5.68 | 4260 | 2 |
| E37 | 5.80 | 1420 | 2 |
| E38 | n.d. | n.d. | n.d. |
| E39 | n.d. | n.d. | n.d. |

Type 1 compounds enhance the effect size of the current elicited by 1 mM choline but minimally alter the kinetics of the receptor. In particular, the rate and the extent of desensitization, elicited by the agonist, is not affected. The compound-modulated response to 1 mM choline, therefore, is a close to linear scaling of the 1 mM choline response in absence of the α7 PAM compound.

Type 2 compounds enhance the effect size of the current elicited by 1 mM choline while reducing the rate and/or the extent of desensitization.

Type 3 compounds enhance the effect size of the current elicited by 1 mM choline. When tested at higher concentrations up to 10 μM they completely inhibit desensitization, in particular a 1 mM choline application of 250 milliseconds.

Type 4 compounds allow for an initial desensitization of the receptor followed by a re-opening of the receptor during agonist application. At low-potency concentrations of the α7 PAM compound, the agonist-induced activation, which is followed by desensitization, can still be separated from the compound-induced re-opening as an initial inward current-maximum. At higher potency concentrations of the α7 PAM compound, the re-opening occurs faster than the closure due to desensitization so that the initial current-maximum disappears.

Surprisingly, the absolute stereochemistry has an impact on the modulation type: in almost all cases the levorotatory compounds, which presumably all have an absolute R configuration, are Type 1 modulators, whereas the corresponding dextrorotatory compounds, which presumably all have an absolute S configuration, are Type 2 modulators. Unexpectedly though, the levorotatory compound E28 is a type 2 modulator, whereas the corresponding dextrorotatory compound E20 is a type 4 modulator.

Example D.3 hERG

The binding affinity of all tested compounds of the present invention at the hERG potassium channel is above 10 μM (pIC$_{50}$<5).

The invention claimed is:
1. A compound according to formula (I)

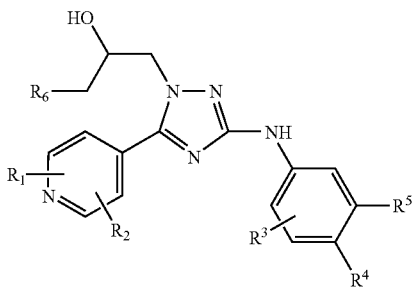

or a stereoisomeric form thereof, wherein
$R^1$ is methyl, ethylamino or methoxyethylamino;
$R^2$ is hydrogen or methyl;
$R^3$ is fluoro, chloro, trifluoromethyl or methyl;
$R^4$ is hydrogen or fluoro;
$R^5$ is hydrogen, fluoro, or methoxy;
$R^6$ is $C_{1-3}$alkyl;
or a pharmaceutically acceptable salt thereof.

2. The compound according to claim 1 or a stereoisomeric form thereof, wherein
$R^1$ is 2-methyl, 2-ethylamino or 2-methoxyethylamino;
$R^2$ is hydrogen or 6-methyl;
$R^3$ is fluoro, chloro, trifluoromethyl or methyl;
$R^4$ is hydrogen or fluoro;
$R^5$ is hydrogen, fluoro, or methoxy;
$R^6$ is $C_{1-3}$alkyl;
or a pharmaceutically acceptable salt thereof.

3. The compound according to claim 1 or a stereoisomeric form thereof, wherein
$R^1$ is 2-methyl, 2-ethylamino or 2-methoxyethylamino;
$R^2$ is hydrogen or 6-methyl;
$R^3$ is fluoro, chloro, trifluoromethyl or methyl;
$R^4$ is hydrogen or fluoro;
$R^5$ is hydrogen, fluoro, or methoxy;
$R^6$ is methyl;
or a pharmaceutically acceptable salt thereof.

4. The compound according to claim 1 wherein the compound is (S)-1-[3-(3,4-difluoro-phenylamino)-5-(2,6-dimethyl-pyridin-4-yl)-[1,2,4]triazol-1-yl]-butan-2-ol, or (R)-1-[3-(3-chloro-phenylamino)-5-(2-ethylamino-pyridin-4-yl)-[1,2,4]triazol-1-yl]-butan-2-ol.

5. A pharmaceutical composition comprising a pharmaceutically acceptable carrier and as active ingredient a therapeutically effective amount of a compound as claimed in claim 1.

6. The pharmaceutical composition of claim 5 wherein the pharmaceutically acceptable carrier and as active ingredient a therapeutically effective amount of a compound as claimed in claim 2.

7. The pharmaceutical composition of claim 5 wherein the pharmaceutically acceptable carrier and as active ingredient a therapeutically effective amount of a compound as claimed in claim 3.

8. The pharmaceutical composition of claim 5 wherein the pharmaceutically acceptable carrier and as active ingredient a therapeutically effective amount of a compound as claimed in claim 4.

* * * * *